US012649858B2

(12) United States Patent
Farmer et al.

(10) Patent No.: US 12,649,858 B2
(45) Date of Patent: Jun. 9, 2026

(54) MATERIALS AND METHODS FOR THE EFFICIENT DISPERSION OF NANOPARTICLES

(71) Applicant: Locus Solutions IPCo, LLC, Solon, OH (US)

(72) Inventors: Sean Farmer, Ft. Lauderdale, FL (US); Ken Alibek, Solon, OH (US); Jonathan Rogers, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 728 days.

(21) Appl. No.: 17/769,880

(22) PCT Filed: Mar. 22, 2021

(86) PCT No.: PCT/US2021/023491
§ 371 (c)(1),
(2) Date: Apr. 18, 2022

(87) PCT Pub. No.: WO2021/189049
PCT Pub. Date: Sep. 23, 2021

(65) Prior Publication Data

US 2022/0411648 A1 Dec. 29, 2022

Related U.S. Application Data

(60) Provisional application No. 62/992,420, filed on Mar. 20, 2020.

(51) Int. Cl.
*C09D 7/00* (2018.01)
*A61K 9/51* (2006.01)
(Continued)

(52) U.S. Cl.
CPC .................. *C09D 7/45* (2018.01); *A61K 9/51* (2013.01); *C05G 3/50* (2020.02); *C09D 5/002* (2013.01); *B82Y 5/00* (2013.01); *B82Y 30/00* (2013.01)

(58) Field of Classification Search
None
See application file for complete search history.

(56) References Cited

U.S. PATENT DOCUMENTS

2002/0143071 A1 10/2002 Gutnick et al.
2009/0238811 A1* 9/2009 McDaniel ................ A61L 2/00 424/94.2

(Continued)

FOREIGN PATENT DOCUMENTS

CN 105567580 A 5/2016
CN 110670385 A 1/2020

(Continued)

OTHER PUBLICATIONS

WO-2020015680-A1—English translation (Year: 2020).*

(Continued)

*Primary Examiner* — Stefanie J Cohen
(74) *Attorney, Agent, or Firm* — BENESCH, FRIEDLANDER, COPLAN & ARONOFF LLP

(57) ABSTRACT

This present invention relates to compositions and methods of enhancing the dispersion of nanoparticles. In certain embodiments, the compositions and methods can be used for enhancing the performance and/or longevity of primers using biochemical-producing microbes and/or byproducts synthesized by the microbes. In certain embodiments, the addition of biosurfactants can enhance the dispersion of pigments and/or other nanoparticles, as well as inhibition of stain or color bleeding through the primer.

18 Claims, 10 Drawing Sheets

(51) Int. Cl.

| | |
|---|---|
| ***C05G 3/50*** | (2020.01) |
| ***C09D 5/00*** | (2006.01) |
| ***C09D 7/45*** | (2018.01) |
| *B82Y 5/00* | (2011.01) |
| *B82Y 30/00* | (2011.01) |

(56) References Cited

U.S. PATENT DOCUMENTS

| | | | | |
|---|---|---|---|---|
| 2011/0118351 | A1 | 5/2011 | Berl | |
| 2011/0139262 | A1 | 6/2011 | Aburto Anell et al. | |
| 2012/0220464 | A1 | 8/2012 | Giessler-Blank et al. | |
| 2013/0296461 | A1 | 11/2013 | Sadasivan | |
| 2014/0205546 | A1 | 7/2014 | Macoviak | |
| 2014/0305649 | A1 | 10/2014 | Tang et al. | |
| 2014/0322428 | A1 | 10/2014 | Wilmott et al. | |
| 2015/0351430 | A1 | 12/2015 | Pipe et al. | |
| 2016/0152525 | A1 | 6/2016 | Chelle et al. | |
| 2017/0056851 | A1 | 3/2017 | Nagano et al. | |
| 2017/0065952 | A1 | 3/2017 | Spyropoulos et al. | |
| 2017/0121671 | A1 | 5/2017 | Firoozmand et al. | |
| 2017/0296496 | A1* | 10/2017 | Morrison ............. | A61K 9/0014 |
| 2020/0140694 | A1* | 5/2020 | Gage ...................... | C08F 220/44 |

FOREIGN PATENT DOCUMENTS

| | | | | |
|---|---|---|---|---|
| CN | 111172786 | A | 5/2020 | |
| JP | 2012232963 | A | 11/2012 | |
| JP | 2012246256 | A | 12/2012 | |
| JP | 2017081907 | A | 4/2017 | |
| KR | 20080030555 | A | 4/2008 | |
| WO | 03031540 | A1 | 4/2003 | |
| WO | 2007130836 | A1 | 11/2007 | |
| WO | 2013164758 | A1 | 11/2013 | |
| WO | 2015137192 | A | 9/2015 | |
| WO | 2017044953 | A1 | 3/2017 | |
| WO | 2018049146 | A1 | 3/2018 | |
| WO | 2018049182 | A2 | 3/2018 | |
| WO | 2018129299 | A1 | 7/2018 | |
| WO | 2018191172 | A1 | 10/2018 | |
| WO | 2018213604 | A3 | 11/2018 | |
| WO | 2019023039 | A2 | 1/2019 | |
| WO | WO-2020015680 | A1 * | 1/2020 | ............. C09K 8/584 |
| WO | 2020069177 | A1 | 4/2020 | |
| WO | 2020096904 | A1 | 5/2020 | |

OTHER PUBLICATIONS

Luft, L., et al., "An overview of fungal biopolymers: bioemulsifiers and biosurfactants compounds production." Critical Reviews in Biotechnology, 40.8 (2020): 1059-1080.

Madankar, C. S., et al., "Review on sophorolipids—a promising microbial bio-surfactant." Tenside Surfactants Detergents, 60.2 (2023): 95-105.

Mulligan, C. N., et al., "Types, Production and Applications of Biosurfactants." Proc. Indian Natn Sci Acad., 2004, B70, 1: 31-55.

Patel, Y., et al., "Biological Treatment of Textile Dyes by Agar-Agar Immobilized Consortium in a Packed Bed Reactor." Water Environment Research, 87.3 (2015): 242-251.

Santos, D. K. F., "Biosurfactants: Multifuctional Biomolecules of the 21st Century." International Journal of Molecular Sciences, 17.3 (2016): 401, pp. 1-31.

Sarubbo, LA., et al., "Some aspects of heavy metals contamination remediation and role of biosurfactants." Chemistry and Ecology, 31.8 (2015): 707-723.

Singh, S., et al., "A direct method for the preparation of glycolipid-metal nanoparticle conjugates: sophorolipids as reducing and capping agents for the synthesis of water re-dispersible silver nanoparticles and their and their antibacterial activity." New Journal of Chemistry, 33.3 (2009) 646-652.

Banat, Ibrahim M., Ravinder S. Makkar, and Swaranjit Singh Cameotra. "Potential commercial applications of microbial surfactants." Applied microbiology and biotechnology 53 (2000): 495-508.

Examination report issued in Indian Patent Application No. 202217057947, dated Nov. 4, 2025.

* cited by examiner

| Primer with Acidic STP | Primer with Lactonic STP |
|---|---|
| 0.05 g/l | 0.05 g/l |
| 0.1 g/l | 0.1 g/l |
| 0.5 g/l | 0.5 g/l |
| 1 g/l | 1 g/l |
| 5 g/l | 5 g/l |

Leneta chart

Paint white for two times

Premium White paint

Just Primer

| Primer with Acetate SLP | Primer with Lactate SLP |
|---|---|
| 0.05 g/l | 0.05 g/l |
| 0.1 g/l | 0.1 g/l |
| 0.5 g/l | 0.5 g/l |
| 1 g/l | 1 g/l |
| 5 g/l | 5 g/l |

Red painted plate

Primer without SLP

Red color of the testing plate is more visible through the thickest coated parts of Control primer.

Layer with Lactonic SLP (0,05 g/l and 0,1 g/l) covered the red surface better.

Red color of the testing plate is more visible through the thickest coated parts of Control primer.

Layer with Lactonic SLP (0,5 g/l and 1 g/l) covered the red surface better.

Red color of the testing plate is more visible through the thickest coated parts of Control primer and primer with Acidic (5g/l) SLP.

Layer with Acidic SLP (1 g/l) covered the red surface better.

Areas where the red paint is seen through the layers of primer and white paint

Areas where the red paint is seen through the layers of primer and white paint

MATERIALS AND METHODS FOR THE EFFICIENT DISPERSION OF NANOPARTICLES

CROSS-REFERENCE TO RELATED APPLICATION

This application is a National Stage Application of International Application No. PCT/US2021/023491, filed Mar. 22, 2021; which claims priority to U.S. Provisional Patent Application No. 62/992,420, filed Mar. 20, 2020, both of which are incorporated herein by reference in their entirety.

BACKGROUND OF THE INVENTION

A nanoparticle is a small particle that is typically characterized as being between 1 to 100 nanometers in size. Nanoparticles, in general, are a large family of both organic and inorganic materials. Each material has uniquely tunable properties and thus can be selectively designed for specific applications. Nanoparticles are undetectable by the human eye, and due to their small size, have a large surface area to volume ratio when compared to bulk material, such as powders, plates and sheets, Properties such as cation exchange capacity, enhanced diffusion, ion adsorption and complexation are enhanced at the nanoscale.

The use of nanomaterials spans across a wide variety of industries, from healthcare and cosmetics, to environmental preservation and materials science. For example, mineral nanoparticles, such as titanium oxide, can be used in sunscreens as UV protection agents with enhanced stability. Nanoparticles can also be used for creating liposome, or nanocapsule, drug delivery systems.

One industry that benefits from nanoparticles is the paint and primer industry. A paint primer is comprised of a mixture of pigments, binders and solvents, or carriers. Ideally, the pigments are evenly dispersed throughout the formulation so that only a thin layer of primer is required to adequately cover a surface.

A universal architectural primer coating serves two main functions. The first is to enhance the ability of a topcoat to beautify the substrate. The second main function is to enhance the durability, extending the life of the topcoat. These functions are primarily achieved by improving adhesion, which can lead to better crack and blister resistance. Additionally, critical performance needs include hiding topographic variations, sealing porous substrates, preventing old colors from showing through the topcoat, odor blocking, providing a tie-coat layer between the surface and topcoat, and reducing stains from migrating into the topcoat.

Examples of nanoparticles used in paints and coatings are titanium dioxide ($TiO_2$), silver (Ag), and silicon dioxide ($SiO_2$). The photocatalytic and hydrophobic properties of titanium dioxide nanoparticles provides for coatings with self-cleaning, air purifying, and anti-UV properties. Nanosilver can have antimicrobial properties, whereas silicon dioxide nanoparticles can increase the scratch- and fire-resistance of paints and coatings.

Zinc nanoparticles are also utilized in primers as undercoats to protect steel surfaces from corrosion in the automotive, marine, chemical plant, oil and gas, industrial machinery and construction industries. Unlike regular paints or epoxies, which resist corrosion by forming impermeable barriers between the metal and atmospheric moisture, zinc rich primers provide additional corrosion protection by electrical means. If the paint is scratched during its operational life, the zinc will sacrificially corrode rather than the steel.

Another industry that benefits from nanoparticles is the oil and gas industry. Adding certain nanoparticles, such as $TiO_2$, CuO, silica-, alumin- and/or carbon-based nanoparticles, to injection solutions can significantly benefit enhanced oil recovery (EOR), with advantages such as wettability alternation, changes in fluid properties, improving mobility of trapped oil, enhancing the consolidation of sands and decreasing the interfacial tension (IFT) in a reservoir. Nanoparticle fluid systems can also be designed for remediation of paraffin and asphaltene deposits, polymers, biofilms and scale, as well as for reducing the viscosity of bitumen and heavy oils.

While nanoparticles have myriad benefits and uses, the formation of solutions having uniform dispersions of nanoparticles remains a challenge. Nanoparticles often form clusters, called aggregates and agglomerates due to, for example, their electrostatic properties. The strength of the bonds can vary, ranging from covalent bonds to weak electrostatic or magnetic forces. For optimum efficacy of nanoparticulate compositions, even distribution of nanoparticles with reduced clustering is ideal. Chemical reagents may be used to force particles to separate; however, more environmentally-friendly methods are desired.

Biosurfactants are chemicals that are part of a growing trend of using microbially-sourced chemicals to replace synthetic chemicals. Biosurfactants are a structurally diverse group of surface-active substances produced by microorganisms. All biosurfactants are amphiphiles. They consist of two parts: a polar (hydrophilic) moiety and non-polar (hydrophobic) group. Due to their amphiphilic structure, biosurfactants can, for example, increase the surface area of hydrophobic water-insoluble substances, increase the water bioavailability of such substances, and reduce interfacial tension at interfaces. Accordingly, because of their environmentally-friendly nature and their wide-ranging uses, biosurfactants have the potential to replace chemicals in a variety of applications and industries.

BRIEF SUMMARY OF THE INVENTION

The subject invention provides materials and methods for improving the dispersion of nanoparticles in compositions utilized in, for example, various industrial, agricultural and healthcare applications. In some embodiments, these applications include, for example, paint and coatings, oil and gas injection fluids, agricultural products, and pharmaceuticals.

In preferred embodiments, nanoparticle compositions are provided, comprising one or more SLP molecules (e.g., acidic SLP (ASL), lactonic SLP (LSL), and/or di-acetylated, mono-acetylated, or esterified forms of SLP) and/or a yeast culture comprising a SLP molecule.

In certain embodiments, the nanoparticle composition comprises one or more nanoparticles, such as, for example, a pigment/dye, a metallic nanoparticle, a polymeric nanoparticle, a liposomal nanoparticle, or another type of nanoparticle known in the art.

In certain embodiments, the present invention utilizes yeast strains and/or byproducts of their growth. The invention provides, for example, a microbe-based product comprising cultivated *Starmerella bombicola* ATCC 22214 and/or products of the growth of that microbe.

In certain embodiments, the yeast in the composition can be inactive and/or in various growth states, such as, for example, vegetative or spore forms.

In one embodiment, the subject invention provides materials and methods for the production of improved primer compositions comprising one or more microbial growth byproducts and/or microbe cultures. The invention also pertains to primer compositions comprising one or more microbial growth byproducts and/or microbe cultures. In certain embodiments, the primer composition comprises SLP molecules and/or a yeast culture comprising an SLP molecule. In certain embodiments, the composition comprises traditional primer ingredients including, for example, solvents, pigments/dyes, buffers, resins, and/or pH modifiers.

In preferred embodiments, methods of improving paint primers are provided, the methods comprising adding a SLP and/or a yeast culture comprising an SLP to the paint primer. In certain embodiments, the addition of the SLP and/or yeast culture enhances the performance and/or longevity of the paint primer upon application to a surface and/or object.

In certain embodiments, the performance of the paint primer can be enhanced by, for example, increasing the primer's adhesion properties, hiding topographic variations of a surface and/or object, sealing porous surfaces and/or objects, preventing colors and/or stains from bleeding through the primer, and/or preventing odor dissemination.

In certain embodiments, the longevity of the paint primer can be enhanced by, for example, increasing the flexibility of the primer.

In certain embodiments, the dispersion of pigments and/or nanoparticles present in the primer composition is enhanced.

Additionally, in preferred embodiments, the improved paint primer can be used to enhance the performance, appearance and/or longevity of an object or surface to which the paint primer is applied. For example, in some embodiments, application of a primer composition according to the subject invention can enhance the longevity of the surface and/or object by preventing fouling by living organisms or non-living substances.

The subject invention further provides injection fluids for the oil and gas industry, wherein nanoparticles are combined with a biosurfactant, such as a sophorolipid. The injection fluids can be introduced into a hydrocarbon-bearing reservoir to, for example, force oil from the formation pores and enhance recovery thereof, remove deposits, and serve as proppant materials for hydraulic fractures.

In another embodiment, the subject invention provides pharmaceutical compositions wherein nanoparticles are combined with a biosurfactant. The pharmaceutical composition can be, for example, a therapeutic agent or a vaccine. In certain embodiments, these compositions have an increased ability to cross the blood-brain barrier (BBB).

In yet another embodiment, the subject invention provides improved agricultural compositions wherein a biosurfactant is combined with a nanoparticle. In preferred embodiments, the nanoparticles comprise nutrients, micronutrients and/or other fertilizers.

In certain embodiments, the subject invention provides environmentally-friendly primer compositions, and methods for use, wherein the compositions can be tailored to possess one or more specific functional properties.

BRIEF DESCRIPTION OF THE FIGURES

FIG. 5A shows primers with 0.05 g/l of lactonic SLP or 0.1 g/l of lactonic SLP; FIG. 5B shows primers with 0.5 g/l of lactonic SLP and 1 g/l of lactonic SLP; FIG. 5C shows primers with 5 g/l of lactonic SLP or 0.05 g/l of acidic SLP; FIG. 5D. shows primers with 0.1 g/l of acidic SLP or 0.5 g/l of acidic SLP; and FIG. 5E shows primers with 1 g/l of acidic SLP or 5 g/l of acidic SLP.

FIG. 6A shows the layer of white paint over the layer of primer with 0.05 g/l of lactonic SLP or 0.1 g/l of lactonic SLP; FIG. 6B shows the layer of white paint over the layer of primer with 0.5 g/l of lactonic SLP or 1 g/l of lactonic SLP; FIG. 6C shows the layer of white paint over the layer of primer with 5 g/l of lactonic SLP or 0.05 g/l of acidic SLP; FIG. 6D shows the layer of white paint over the layer of primer with 0.1 g/l of acidic SLP or 0.5 g/l of acidic SLP; and FIG. 6E shows the layer of white paint over the layer of primer with 1 g/l of acidic SLP or 5 g/l of acidic SLP.

DETAILED DESCRIPTION OF THE INVENTION

Figure 1:
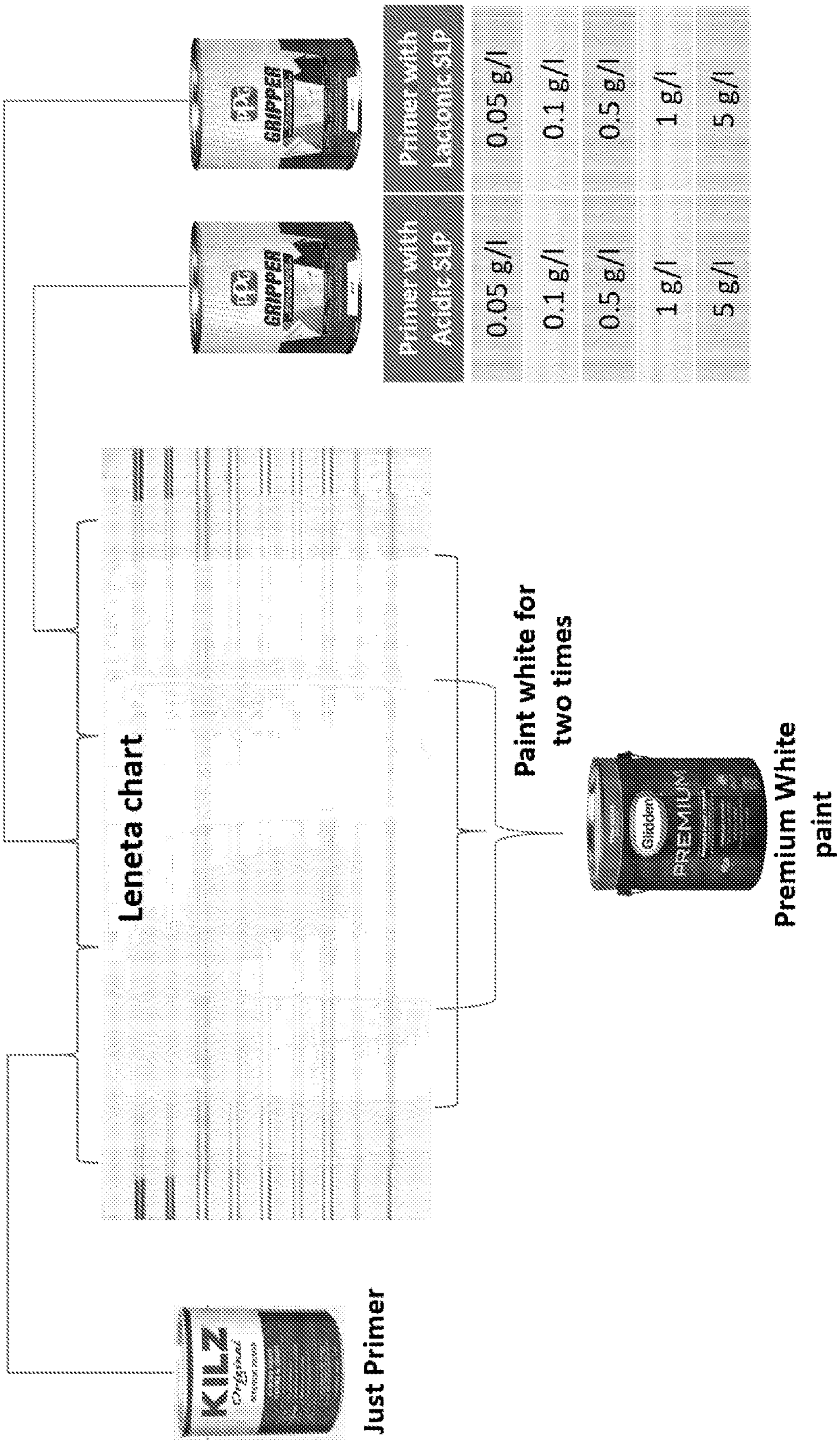
FIG. 1 shows a schematic of how the primer or the paint and primer were applied to a Leneta drawdown chart. Kilz primer was applied to the left column of the chart. Gripper primer with 0.05 g/l, 0.1 g/l, 0.5 g/l, 1 g/l, or 5 g/l of either acidic or lactonic SLP was applied to the center column or the right column. A single layer of white paint was applied to the area encompassed by the red bracket, creating the Leneta drawdown charts of FIG. 2, After the first layer of paint dried, a second, narrower column of paint was applied to the chart in the area encompassed by the blue bracket beneath the Leneta chart, creating the Leneta charts of FIG. 3.

The present invention provides materials and methods for improving nanoparticle compositions. Specifically, the subject invention provides materials and methods for the production of nanoparticle compositions comprising one or more microbial growth byproducts and/or microbe cultures. The invention also pertains to nanoparticle compositions comprising one or more microbial growth byproducts and/or microbe cultures. In certain embodiments, the composition can comprise SLP molecules and/or a yeast culture comprising an SLP molecule.

The nanoparticle compositions can be useful for improving any of the following exemplary areas in which nanoparticles are used:

| | |
|---|---|
| 3D printing | Molecular Tagging |
| Textiles | MRI contrast agents |
| Biomedical formulations and research | IR contrast agents |
| Health care | Antioxidants |
| Food production | Gas-Barrier Coating |
| Agriculture | Self-Cleaning Building surfaces |
| Industrial formulations | Nanophosphors for display |
| Electronics | Superplastic ceramics |
| Environment | Chemical mechanical planarization |
| Renewable energy | High sensitivity sensors |
| Drug delivery | Quantum lasers |
| Cancer therapeutic delivery | Pollution monitoring sensors |
| Antibacterials | Automotive catalysts |
| Fungicides | Fuel additive catalysts |
| UV protection | Dye sensitized solar cells |
| UV blocking textiles | Paint-on solar cells |
| Sunscreen | Self-cleaning textiles |
| Food packaging | Nutraceuticals |
| Industrial Catalysts | Functional food |
| Quantum Computers | Reinforced plastics |
| Wastewater Treatment | Nano-scale patterning of electronic |
| Hydrogen production photocatalysts | circuits |
| Lithium ion battery electrodes | High density data storage |
| Medical textiles | Fuel cell catalysis |
| Bone growth | Oil and gas recovery |

In a specific embodiment, the subject invention provides primer compositions that, for example, increase performance, appearance, and/or longevity of an object and/or surface, are provided, wherein the primer compositions comprise SLP molecules (e.g., acidic SLP (ASL), lactonic SLP (LSL), and/or di-acetylated, mono-acetylated, or esterified forms of SLP) and/or yeast cultures, in addition to one or more traditional primer ingredients.

Selected Definitions

As used herein, enhancing the "dispersion" of nanoparticles means promoting a substantially even or uniform distribution of nanoparticles suspended throughout a fluid. Promoting a substantially even distribution means reducing the degree to which the nanoparticles cluster together into agglomerates and/or aggregates and/or reducing the size and/or number of such clusters. An agglomerate is a reversible collection of particles that are weakly bound by, for example, van der Waals forces, whereas an aggregate is comprised of particles held together by stronger covalent bonds.

In some embodiments, the degree of dispersion of the nanoparticles in a composition produced according to the subject invention can be measured by, for example, the zeta potential, where suspensions possessing a high absolute value of zeta potential are considered "well-dispersed." See Fairhurst 2013, incorporated by reference herein.

As used herein, the term "sophorolipid," "sophorolipid molecule," "SLP" or "SLP molecule" includes all forms, and isomers thereof, of SLP molecules, including, for example, acidic (linear) SLP (ASL) and lactonic SLP (LSL). Further included are all possible derivatives of SLP molecules, including, for example, mono-acetylated SLP, di-acetylated SLP, esterified SLP, SLP with varying hydrophobic chain lengths, SLP with fatty acid-amino acid complexes attached, and others as are described within in this disclosure.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. The microbes may be present in or removed from the composition. The microbes can be present, with broth in which they were grown, in the microbe-based composition. The cells may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$, or more CFU per milliliter of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, a "biofilm" is a complex aggregate of microorganisms, such as bacteria, wherein the cells adhere to each other and/or to a surface using an extracellular polysaccharide matrix. The cells in biofilms are physiologically distinct from planktonic cells of the same organism, which are single cells that can float or swim in liquid medium.

As used herein, "harvested" refers to removing some or all of a microbe-based composition from a growth vessel.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. An isolated microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight the compound of interest. Preferably, the preparation is at least 75%, more preferably at least 90%, and most preferably at least 98%, by weight the compound of interest. For example, a purified compound is one that is at least 80%, 85%, 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism or a substance necessary for taking part in a particular metabolic process. A metabolite can be an organic compound that is a starting material, an intermediate in, or an end product of metabolism. Examples of metabolites include, but are not limited to, enzymes, acids, solvents, alcohols, proteins, vitamins, minerals, microelements, amino acids, biopolymers and biosurfactants.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19 and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein a "reduction" means a negative alteration, and an "increase" means a positive alteration, wherein the negative or positive alteration is at least 0.001%, 0.01%, 0.1%, 0.5%, 1%, 5%, 10%, 15%, 20%, 25%, 30%, 35%, 40%, 45%, 50%, 55%, 60%, 65%, 70%, 75%, 80%, 85%, 90%, 95% or 100%.

As used herein, "surfactant" means a compound that lowers the surface tension (or interfacial tension) between two liquids or between a liquid and a solid. Surfactants act as, e.g., detergents, wetting agents, emulsifiers, foaming agents, and/or dispersants. A "biosurfactant" is a surface-active substance produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially or limits the scope of" a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, a "primer," "undercoat," "paint primer," or "architectural primer" is a coating that is initially applied to an object or surface in preparation for the application of a "finishing coat." The finishing coating can be materials such as, for example, paints, stains, varnishes, or lacquers, which are designed for use as a protective layer or a means to add color or texture. The primer is traditionally designed to increase adhesion of the finishing coat to the surface, increase longevity of finishing coat, or add additional protective properties.

As used herein, a "tie-coat layer" is a layer of material that acts as a bridge between the undercoat and the finished coating layer. A tie-coat layer bonds or improves adhesion of layers to each other or of a layer to the surface to which it is applied.

As used herein, a "resin" means a highly viscous or solid compound, preferably of synthetic origin, that can be used in primer compositions to solidify the primer upon application.

As used herein, the term "flexibility," in the context of primer compositions, refers to the ability of the primer to move or bend, including from the expansion or retraction of the object to which it is applied, without cracking or blistering.

According to the subject invention, a harmful accumulation of material, including living organisms or non-living substances results in the process of "fouling." "Fouling" can result in clogging, scaling, or other undesired buildup. "Fouling" can affect the efficiency, reliability, or functionality of the object.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Nanoparticle Compositions

In preferred embodiments, the subject invention provides improved nanoparticle compositions comprising one or more microbial growth by-products and/or microbial cultures, in addition to one or more nanoparticle ingredients.

In certain embodiments, the compositions and methods according to the subject invention utilize sophorolipid biosurfactants and/or yeast cultures comprising sophorolipids, in addition to the one or more traditional primer ingredients.

The SLP of the composition can be, for example, a lactonic, linear, mono-acetylated lactonic or linear, and/or di-acetylated lactonic or linear sophorolipid. In certain embodiments, the composition comprises more than one SLP molecule.

Sophorolipids are glycolipid biosurfactants produced by, for example, various yeasts of the *Starmerella* clade. SLP consist of a disaccharide sophorose linked to long chain hydroxy fatty acids. They can comprise a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. Furthermore, the sophorose residue can be acetylated on the 6- and/or 6'-position(s). The fatty acid carboxyl group can be free (acidic or linear form (General Formula 1)) or internally esterified at the 4"-position (lactonic form (General Formula 2)). *S. bombicola* produces a specific enzyme, called *S. bombicola* lactone esterase, which catalyzes the esterification of linear SLP to produce lactonic SLP.

(1)

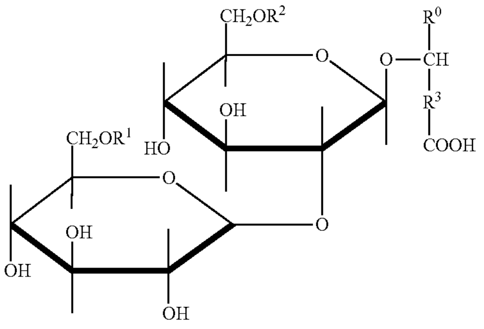

(2)

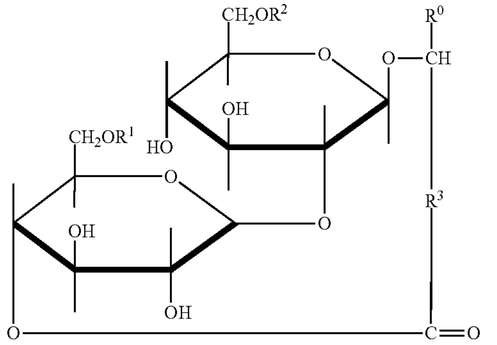

where $R^1$ and $R^{1'}$ independently represent saturated hydrocarbon chains or single or multiple, in particular single, unsaturated hydrocarbon chains having 8 to 20, in particular 12 to 18 carbon atoms, more preferably 14 to 18 carbon atoms, which can be linear or branched and can comprise one or more hydroxy groups, $R^2$ and $R^{2'}$ independently represent a hydrogen atom or a saturated alkyl functional group or a single or multiple, in particular single, unsaturated alkyl functional group having 1 to 9 carbon atoms, more preferably 1 to 4 carbon atoms, which can be linear or branched and can comprise one or more hydroxy groups, and $R^3$, $R^{3'}$, $R^4$ and $R^{4'}$ independently represent a hydrogen atom or an acetyl group.

Due to the structure and composition of SLP, these biosurfactants have excellent surface and interfacial tension reduction properties, as well as other beneficial biochemical properties, which can be useful as a replacement for chemical surfactants in applications such as large scale industrial and agriculture uses, cosmetics, household products, health, medical and pharmaceutical fields, and oil and gas recovery.

The sophorolipid may be in a purified form or in a mixture of fermentation products. The sophorolipid may be added at concentrations of 0.01 to 90% by weight (wt %), preferably 0.1 to 50 wt %, and more preferably 0.1 to 20 wt %. In another embodiment, purified SLP may be in combination with an acceptable carrier, in that SLP may be presented at concentrations of 0.001 to 50% (v/v), preferably, 0.01 to 20% (v/v), more preferably, 0.02 to 5% (v/v).

In certain embodiments, the biosurfactant content of the subject invention ranges from about 0.0001% to 99.9% wt %, 0.001% to 90%, 0.01% to 85%, 0.015% to 80%, 0.1% to 75%, 0.15% to 70%, 0.2% to 65%, 0.25% to 60%, 0.3% to 55%, 0.35% to 50%, 0.4% to 45%, 0.45% to 40%, 0.5% to 35%, 0.55% to 30%, 0.6% to 25%, or 0.65% to 20% wt %.

In certain embodiments, the size of a biosurfactant molecule and/or a micelle according to the subject invention is less than 10 nm, preferably less than 8 nm, more preferably less than 5 nm. In a specific embodiment, the size is from 0.8 nm to 1.5 nm, or about 1.0 to 1.2 nm. Advantageously, such small size allows for enhanced penetration of biosurfactants into nanometer-sized spaces and pores, such as those in subterranean oil-bearing formations, between plant and animal cells, in cell membranes, and in biofilm matrices.

The subject invention utilizes methods for cultivation of microorganisms and production of microbial metabolites and/or other byproducts of microbial growth. The microbial cultivation systems would typically use submerged culture fermentation; however, surface culture and hybrid systems can also be used. As used herein "fermentation" refers to growth of cells under controlled conditions. The growth could be aerobic or anaerobic.

The microorganisms utilized according to the subject invention may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation. missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microorganism is any yeast or fungus. Examples of yeast and fungus species suitable for use according to the current invention, include, but are not limited to, *Acaulospora, Aspergillus, Aureobasidium* (e.g., *A. pullulans*), *Blakeslea, Candida* (e.g., *C. albicans, C. apicola*), *Cryptococcus, Debaryomyces* (e.g., *D. hansenii*), *Entomophthora, Fusarium, Hanseniaspora* (e.g., *H, uvarum*), *Hansenula, Issatchenkia, Kluyveromyces, Mortierella, Mucor* (e.g., *M. piriformis*), *Meyerozyma* (e.g., *M. guilliermondii*), *Penicillium, Phythium, Phycomyces, Pichia* (e.g., *P. anomala, P. guilliermondii, P. occidentalis, P. kudriavzevii*), *Pseudozyma* (e.g., *P. aphidis*), *Rhizopus, Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T virens*), *Ustilago* (e.g., *U. maydis*), *Wickerhamomyces* (e.g., *W. anomalus*), *Williopsis*, and *Zygosaccharomyces* (e.g., *Z. bailii*).

In certain embodiments, the microorganism is a *Starmerella* spp. yeast and/or *Candida* spp. yeast, e.g., *Starmerella* (*Candida*) *bombicola, Candida apicola, Candida batistae, Candida floricola, Candida riodocensis, Candida stellate* and/or *Candida kuoi*. In a specific embodiment, the microorganism is *Starmerella bombicola*, e.g., strain ATCC 22214.

In one embodiment, the subject invention provides materials and methods for the production of biomass (e.g. viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g. measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method of cultivation can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil. These carbon sources may be used independently or in a combination of two or more.

In one embodiment, growth factors and trace nutrients for microorganisms are included in the medium. In one embodiment, inorganic salts may also be included. In certain embodiments, the method for cultivation may further comprise adding additional acids and/or antimicrobials in the liquid medium before, and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

The biomass content of the fermentation broth may be, for example from 5 g/l to 180 g/l or more. In one embodiment, the solids content of the broth is from 10 g/l to 150 g/l.

In one embodiment, the primer compositions comprise a yeast culture produced according to the subject methods.

In one embodiment, the subject invention further provides a method for producing microbial metabolites such as ethanol, lactic acid, beta-glucan, proteins, peptides, metabolic intermediates, polyunsaturated fatty acids, biosurfactants, and lipids. The metabolite content produced by the method can be, for example, at least 20%, 30%, 40%, 50%, 60%, 70%, 80%, or 90%.

The microbial growth byproduct produced by microorganisms of interest may be retained in the microorganisms or secreted into the liquid medium. In another embodiment, the method for producing microbial growth byproduct may further comprise steps of concentrating and purifying the microbial growth byproduct of interest. In a further embodiment, the liquid medium may contain compounds that stabilize the activity of microbial growth byproduct.

In preferred embodiments, the microbial growth byproduct is a biosurfactant. Specific biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

In one embodiment, the microbial biosurfactant is a glycolipid such as a rhamnolipid (RLP), sophorolipid (SLP), trehalose lipid or mannosylerythritol lipid (MEL). In one embodiment, the microbial biosurfactant is a lipopeptide, such as an iturin, a fengycin or a surfactin.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Advantageously, the microbe-based products can be produced in remote locations. The microbe growth facilities may operate off the grid by utilizing, for example, solar, wind and/or hydroelectric power.

In some embodiments, the nanoparticle ingredient of the subject composition has a size from about 0.5 to about 1,000 nanometers, about 1 to about 750 nanometers, about 1.5 to about 500 nanometers, about 2 to about 250 nanometers, or about 2.5 to about 150 nanometers.

In some embodiments, the size of a nanoparticle refers to the diameter or approximate diameter of a nanoparticle. For a population of nanoparticles, this can also be referred to as a Z-average particle size, which can be measured according to routine protocols known to one skilled in the art.

In some embodiments, the size is measured by dynamic light scattering (DLS) (Z-average). In some embodiments, the size is measured by TEM (Transmission Electron Microscopy).

In some embodiments, the total amount of the nanoparticle ingredient in the composition is from about 0.001 wt % to about 50 wt %, about 0.01 wt % to about 25 wt %, about 0.05 wt % to about 20 wt %, about 0.1 wt % to about 15 wt %, about 0.5 wt % to about 10 wt %, or about 1 wt % to about 5 wt % of the total composition.

Exemplary types of nanoparticle ingredients according to the subject invention can include, for example, liposome-based nanoparticles, metallic nanoparticles, polymeric nanoparticles, inorganic nanoparticles, viral nanoparticles, lipid-based nanoparticles, nanoparticle albumin-bound technology, quantum dots, nano-tubes, inorganic semiconductor nanocrystals, metallic nanospheres, and others known in the art.

In one embodiment, the nanoparticle composition can comprise positively and negatively charged nanoparticles at a ratio of 1:10 to 10:1, positively charged to negatively charged.

In certain embodiments, the nanoparticle ingredient(s) can comprise, for example, positively and/or negatively-charged ions; Aluminum Cerium Oxide Nanoparticles; Aluminum Hydroxide Nanoparticles; Aluminum Hydroxide Oxide Nanoparticles; Aluminum; Aluminum Nanoparticles; Aluminum Nitride Nanoparticles; Aluminum Oxide Nanoparticles; Aluminum Oxide Nanoparticles, Silane Coated; Aluminum Titanate Nanoparticles; Aluminum-doped Zinc Oxide Nanoparticles; Antimony Nanoparticles; Antimony Oxide Nanoparticles; Antimony Tin Oxide (ATO) Nanoparticles; Arsenic Oxid; anoparticles; Barium Iron Oxide Nanoparticles; Barium Oxide Nanoparticles; Barium Strontium Titanate Nanoparticles; Barium Sulfate Nanoparticles; Barium Titanate Nanopowder; Barium Zirconate Nanoparticles; Beryllium Nanoparticles; Beryllium Oxide Nanoparticles; Bismuth Cobalt Zinc Oxide Nanoparticles; Bismuth Nanoparticles; Bismuth Oxide Nanoparticles; Boron Carbide Nanoparticles; Boron Nanoparticles; Boron Nitride Nanoparticles; Boron Oxide Nanoparticles; Cadmium Oxide Nanoparticles; Calcium Carbonate Nanoparticles; Calcium chloride nanoparticles; Calcium Hydrogen Phosphate Nanopowder; Calcium Oxide Nanoparticles; Calcium Phosphate Nanoparticles; Calcium Titanate Nanoparticles; Calcium Zirconate Nanoparticles; Carbon Black Nanoparticles; Carbon Nanoparticles; Carbon nanotubes; Cerium Nanoparticles; Cerium Oxide, Calcium doped Nanopowder; Cerium Oxide, Gadolinium doped Nanopowder; Cerium Oxide, Samarium doped Nanopowder; Cerium Oxide, Yttria doped Nanopowder; Cerium Zirconium Oxide Nanoparticles; Cesium Oxide Nanoparticles; Chromium Carbide Nanoparticles; Chromium Cobalt Iron Nanoparticles; Chromium Nanoparticles; Chromium Nitrate Nanopowder; Chromium Oxide Nanoparticles; CIS Nanoparticles; C-MITE Cerium Oxide Nanoparticles; Cobalt Aluminum Oxide Nanoparticles; Cobalt Iron Nanoparticles; Cobalt Iron Oxide Nanoparticles; Cobalt Iron Oxide Nanoparticles; Cobalt Iron Zinc Oxide Nanoparticles; Cobalt Nanoparticles; Cobalt(II) Oxide Nanoparticles; Cobalt(II,III) Oxide Nanoparticles; Cobalt(III) Oxide Nanoparticles; Copper Aluminum Oxide Nanoparticles; Copper Indium Gallium Selenide Nanoparticles; Copper Iron Oxide Nanoparticles; Copper Nanoparticles; Copper Nickel Nanoparticles; Copper Oxide Nanoparticles; Copper Tin Alloy Nanoparticles; Copper Zinc Iron Oxide Nanoparticles; Copper Zinc Nanoparticles; Copper-Zinc Alloy Nanopowder; Diamond Nanoparticles; Dysprosium Nanoparticles; Dysprosium Oxide Nanoparticles; Erbium Nanoparticles; Europium Nanoparticles; Europium Oxide Nanoparticles; Ferrofluid; Fullerene Powder; Gadolinium Nanoparticles; Gadolinium Oxide Nanoparticles; Gallium Antimonide Nanoparticles; Gallium Arsenide Nanoparticles; Gallium Nitrate Nanoparticles; Gallium Oxide Nanoparticles; Gallium-doped Zinc Oxide Nanoparticles; Germanium Nanoparticles; Germanium Oxide Nanoparticles; Gold Nanoparticles; Gold Nanoparticles on Carbon Black; Gold Nanoparticles on Titania; Gold Oxide Nanoparticles; Graphite Nanoparticles; Hafnium Nanoparticles; Hafnium Oxide Nanoparticles; Holmium Nanoparticles; Holmium Oxide Nanopowder; Hydroxyapatite Nanoparticles; Indium Hydroxide Nanoparticles; Indium Nanoparticles; Indium Oxide Nanoparticles; Indium Phosphide Nanoparticles; Indium Tin Oxide Nanoparticles; Iridium Nanoparticles; Iridium Oxide Nanoparticles; Iron Cobalt Nanopowder; Iron Hydroxide Oxide Nanoparticles; Iron Nanoparticles; Iron Nickel Copper Nanoparticles; Iron Nickel Nanoparticles; Iron Nickel Oxide Nanoparticles; Iron(II,III) Oxide Nanoparticles; Iron(III) Oxide Nanoparticles; Lanthanum Hexaboride Nanoparticles; Lanthanum Nanoparticles; Lanthanum Nickelate Nanoparticles; Lanthanum Nickelate, Strontium Doped Nanopowder; Lanthanum Oxide Nanoparticles; Lanthanum Strontium Manganese Oxide Nanoparticles; Lanthanum Strontium Manganite Nanopowder; Lanthanum Trifluoride Nanoparticles; Lead Nanoparticles; Lead Oxide Nanoparticles; Lithium Carbonate Nanoparticles; Lithium Cobalt Oxide Nanoparticles; Lithium Iron Phosphate Nanoparticles; Lithium Manganese Oxide Nanoparticles; Lithium Nanoparticles; Lithium Oxide Nanoparticles; Lithium Titanate Nanoparticles; Lithium Titanate Spinel, Nanopowder; Lithium Vanadate Nanoparticles; Lutetium Nanoparticles; Lutetium Oxide Nanoparticles; Magnesium Aluminate, Spinel Nanoparticles; Magnesium Aluminum Oxide Nanoparticles; Magnesium Hydroxide Nanoparticles; Magnesium Iron Oxide Nanoparticles; Magnesium Nanoparticles; Magnesium Oxide Nanoparticles; Magnesium Zinc Iron Oxide Nanoparticles; Manganese Iron Oxide Nanoparticles; Manganese Nanoparticles; Manganese Oxide Nanoparticles; Manganese Titanium Oxide Nanoparticles; Manganese Zinc Iron Oxide Nanoparticles; Molybdenum Carbide Nanopowder; Molybdenum Nanoparticles; Molybdenum Oxide Nanoparticles; Molybdenum Sulfide Nanoparticles; Neodymium Nanoparticles; Neodymium Oxide Nanoparticles; Nickel Chromium Oxide Nanoparticles; Nickel Cobalt Chromium Nanoparticles; Nickel Cobalt Iron Oxide Nanoparticles; Nickel Cobalt Oxide Nanoparticles; Nickel Hydroxide Nanoparticles; Nickel Nanoparticles; Nickel Oxyhydroxide Nanopowder; Nickel Titanium Nanopowder; Nickel Zinc Iron Oxide Nanoparticles; Nickel(II) Oxide Nanoparticles; Nickel(III) Oxide Nanoparticles; Niobium Boride Nanoparticles; Niobium Carbide Nanoparticles; Niobium Nanoparticles; Niobium Nitride Nanoparticles; Niobium Oxide Nanoparticles; Osmium Nanoparticle; Osmium Oxide Nanoparticles; Palladium Nanoparticles; Palladium Nanoparticles Entrapped in Aluminum Hydroxide Matrix; Palladium Oxide Nanoparticles; Platinum Nanoparticles; Platinum Nanoparticles on Carbon Black; Platinum Nanoparticles on Titania; Platinum Oxide Nanoparticles; Potassium Oxide Nanoparticles; Praseodymium Nanoparticles; Praseodymium Oxide Nanoparticles; Rhenium Nanoparticles; Rhenium Oxide Nanoparticles; Rhodium Nanoparticles Entrapped in Aluminum Hydroxide Matrix; Rhodium Oxide Nanoparticles; Rubidium Oxide Nanoparticles; Ruthenium Nanoparticles; Ruthenium Oxide Nanoparticles; Samarium Nanoparticles; Samarium Oxide Nanoparticles; Samarium Strontium Cobalt Oxide Nanoparticles; Scandium Nanoparticles; Scandium Oxide Nanoparticles; Selenium Nanoparticles; Selenium Oxide Nanoparticles; Silica; Silicon Aluminum Nanoparticles; Silicon Carbide Nanoparticles; Silicon Carbide Nitride Nanopowder; Ruthenium Oxide Nanoparticles; Silicon Nanoparticles; Silicon Nitride Nanoparticles; Silicon Oxide Nanoparticles; Silver Copper Nanopowder; Silver Nanoparticles; Silver Oxide Nanoparticles; Silver Platinum Nanoparticles; Silver Tin Alloy Nanoparticles; Sodium Oxide Nanoparticles; Stainless Steel Nanoparticles; Strontium Aluminum Oxide Nanoparticles; Strontium Carbonate Nanoparticles; Strontium Ferrite Nanoparticles; Strontium Iron Oxide Nanoparticles; Strontium Nanoparticles; Strontium Oxide Nanoparticles; Strontium Titanate Nanoparticles; Sulfur Nanoparticles; Tantalum Carbide Nanoparticles; Tantalum Nanoparticles; Tantalum Oxide Nanoparticles; Tellurium Nanoparticles; Tellurium Oxide Nanoparticles; Terbium Nanoparticles; TErbium Oxide Nanoparticles; Thallium Nanoparticles; Thallium Oxide Nanoparticles; Thorium Oxide Nanopowder; Thulium Nanoparticles; Thulium Oxide Nanoparticles; Tin Nanoparticles; Tin Oxide Nanopowder; Tin Silver Copper Nanoparticles; Titanium Boride Nanoparticles; Titanium Boride-Boron Carbide Nanoparticles; Titanium Boride-Boron Carbide-Tungsten Boride Nanoparticles; Titanium Boron Oxide Nanoparticles; Titanium Boride Nanoparticles; Titanium Carbide Nanoparticles; Titanium Carbon Nanoparticles; Titanium Carbon Nitrate Nanoparticles; Titanium Carbonitride Nanoparticles; Titanium Nanoparticles; Titanium Nitride Nanoparticles; Titanium Oxide Nanoparticles; Anatase Nanopowder; Titanium Dioxide, Rutile Nanopowder; Titanium Silicate Nanoparticles; Titanium(IV) Oxide, Mixture of Rutile and Anatase Nanoparticles; Tungsten Carbide-Cobalt Nanoparticles; Tungsten Carbide Nanoparticles; Tungsten Disulfide Nanoparticles; Tungsten Nanoparticles; Tungsten Oxide Nanopowder; Tungsten Sulfide Nanoparticles; Vanadium Carbide Nanoparticles; Vanadium Nanoparticle; Vanadium Nitride Nanoparticles; Vanadium Oxide Nanoparticles; Ytterbium Fluoride Nanoparticles; Ytterbium Nanoparticles; YttErbium Oxide Nanoparticles; Yttria Stabilized Zirconia Nanoparticles; Yttria Stabilized Zirconia Nanoparticles; Yttrium Aluminate Nanoparticles; Yttrium Aluminum Oxide Nanoparticles; Yttrium Europium Oxide Nanoparticles; Yttrium Iron Oxide Nanoparticles; Yttrium Nanoparticles; Yttrium Oxide Nanoparticles; Zinc Iron Oxide Nanoparticles; Zinc Nanoparticles; Zinc Oxide Nanoparticles; Zinc Titanate Nanoparticles; Zirconium Carbide Nanopowder; Zirconium Hydroxide Nanoparticles; Zirconium Nanoparticles; Zirconium Nitrate Nanoparticles; Zirconium Oxide Nanoparticles; and Zirconium(IV) Silicate Nanoparticles;

Carbon Black Nanopowder; Carbon Electrodes; Carbon Fabric; Carbon Fiber; Carbon Foam; Carbon Granules; Carbon Nanoparticles; Carbon Nanorods; Carbon Nanotube Ink; Carbon Nanotubes; Carbon Pieces; Carbon Powder; Carbon Slugs; Copper Carbon Nanotubes; Double-Walled Carbon Nanotubes; Graphene; 3D Graphene Foam; Graphene Monolayer; Graphene Multilayer; Graphene Nanoplatelets; Graphene Oxide Monolayer; Graphene Oxide Paper; Graphene Oxide Thin Film; Graphite Nanofibers; Graphite Nanopowder; Graphite Paste; Graphite Powder; Graphite Precipitate; Graphite Rod; Graphite Shavings; Graphite, Expandable; Graphite, Fluorinated, Polymer; Graphite, Micronized; Graphite, Natural Amorphous; Graphite, Natural Flake; Graphite, Spherical; Lithium Titanate; Manganese Selenide; Mesoporous Carbon; Multi-Walled Carbon Nanotubes; Potassium Graphite; Pyrolytic Graphite; and Tunable Nanoporous Carbon; and Pigments, Ag NPs/Ag ions, TiO2 nanoparticles, Metal-doped TiO2, Titanate nanotubes, Binary mixed oxide, Iron-based, and Bimetallic nanoparticles.

Preparation of Yeast-Based Products

One yeast-based product of the subject invention is simply the fermentation broth containing the yeast and/or the microbial metabolites produced by the yeast and/or any residual nutrients. The product of fermentation may be used directly without extraction or purification. If desired, extraction and purification can be easily achieved using standard extraction and/or purification methods or techniques described in the literature.

The yeasts in the yeast-based product may be in an active or inactive form, or a mixture thereof. The yeast-based products may be used without further stabilization, preservation, and storage. Advantageously, direct usage of these yeast-based products preserves a high viability of the microorganisms, reduces the possibility of contamination from foreign agents and undesirable microorganisms, and maintains the activity of the byproducts of microbial growth.

In one embodiment, the yeast fermentation product can be obtained via cultivation of the biosurfactant-producing yeast, *Starmerella bombicola*. This species is an effective producer of glycolipid biosurfactants, such as SLP. The fermentation broth after 5 days of cultivation at 25° C. can contain the yeast cell suspension and, for example, 150 g/L or more of glycolipid biosurfactants.

In specific embodiments, the biosurfactants of the subject composition comprise one or more glycolipid biosurfactants. In specific preferred embodiments, the glycolipid is a sophorolipid.

The yeast and/or broth resulting from the yeast growth can be removed from the growth vessel and transferred via, for example, piping for immediate use.

The yeast fermentation product can comprise yeast cells and fermentation broth, or it can comprise the fermentation broth separated from the yeast cells. In one embodiment, the biosurfactants or other growth byproducts in the broth are further separated from the broth and purified.

In other embodiments, the composition (yeast, broth, or yeast and broth) can be placed in containers of appropriate size, taking into consideration, for example, the intended use, the contemplated method of application, the size of the fermentation tank, and any mode of transportation from microbe growth facility to the location of use. Thus, the containers into which the yeast-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier); the presence of biopolymer beta-glucan (an emulsifier) in yeast cell walls; and the presence of biosurfactants, metabolites and solvents (e.g., lactic acid, ethanol, ethyl acetate, etc.) in the culture.

Other biosurfactants and solvents that are useful according to the present invention include mannoprotein, beta-glucan, ethanol, lactic acid and other metabolites that have, for example, bio-emulsifying and surface/interfacial tension-reducing properties.

Upon harvesting the yeast-based composition from the growth vessels, further components can be added as the harvested product is placed into containers and/or piped (or otherwise transported for use). The additives can be, for example, dyes, pigments, pH adjusting agents, buffers, salts, adhesion-promoting compounds, solvents (e.g., isopropyl alcohol, ethanol), biocides, other microbes, and other ingredients specific for an intended use. In certain embodiments, the composition of the subject invention comprises a binder, primarily responsible for adhesion of the primer to an object. The binder compounds can be selected from, for example, acrylic, alkyds, acrylic acid, acrylamide, phenolic, phenolic-alkyd, polyacrylamide, polyurethanes, silicone-alkyd, polyesters, epoxies, vinyl, vinyl acetate-ethylene, vinyl-alkyd, inorganic binders (sodium, potassium ethyl silicate, lithium, etc.), organic binders (carbon-based), Tectyl® (Daubert Chemical Company, Inc., Chicago, IL), aliphatic-urethanes, and oil-modified urethanes.

In certain embodiments, the primer composition of the subject invention comprises a pigment or dye, which can provide the color to the primer. Pigments or dyes can be natural, synthetic, inorganic, or organic. The pigments or dyes can be selected from, for example, titanium dioxide, zinc oxide, zinc yellow, yellow dyes, benzidine yellows, chrome oxide green, phthalocyanine green, phthalocyanine blue, ultramarine blue, vermillion, pigment brown 6, red 170, dioxazine violet, carbon black, iron (II) oxide, quartz sand ($SiO_2$), talc, barite ($BaSO_4$), kaolin clay, and limestone ($CaCO_3$).

In certain embodiments, the composition comprises a solvent selected from mineral or organic solvents, including, for example, ethanol, butanol, propanol, aliphatic hydrocarbons, alicyclic hydrocarbons, xylene, toluene, d-limonene, ketones, and/or isopropyl alcohol. In a preferred embodiment, isopropyl alcohol in an amount of 1 to 100 ml/L, more preferably from 2 to 50 ml/L, is added as to the composition.

In certain embodiments, the composition further comprises water as solvent. The water can be filtered by granular-activated carbon, deionized, distilled, or processed by reverse osmosis. Additionally, pH modifiers can be used to increase or decrease the pH to, preferably, facilitate the dissolution of various components of the primer compositions. The water-based primer compositions can be acrylic-based or latex-based. The latex can be from a natural origin, such as, for example, a flowering plant (angiosperm), or, preferably, the latex is synthetically derived from, for example, polymerizing styrene. The acrylic base for a primer can be created from acrylic resins, which are synthetic thermoplastics.

In certain embodiments, the primer can be oil-based. Synthetic or natural resins can be used in combination with any one of the aforementioned solvents to create the oil-based resin. Alkyd resins can be, for example, used in the subject composition. Alkyd resins can be created using natural oils, such as, for example, linseed oil, safflower oil, soybean oil, sunflower oil, tung oil, or castor oil.

In one embodiment, the yeast-based product may further comprise buffering agents including organic and amino acids or their salts. Suitable buffers include, for example, citrate, gluconate, tartrate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used, but it is preferable to use natural buffers such as organic and amino acids or their salts listed above.

In a further embodiment, pH modifying agents include potassium hydroxide, ammonium hydroxide, potassium carbonate or bicarbonate, hydrochloric acid, nitric acid, sulfuric acid or a mixture.

The yeast-based product may be applied with a composition that promotes adherence of the yeast-based product to a surface to be treated. The adhesion-promoting substance may be a component of the yeast-based product or it may be applied simultaneously or sequentially with the yeast-based product. Examples of useful adhesion promoters include maleic acid, crotonic acid, fumaric acid, polyesters, polyamides, polyethers, polyacrylates and polyurethanes.

Other additives that can used in the subject compositions include water softening agents, sequestrants, corrosion inhibitors, non-biological surface-active agents, detergents, crystal modifiers, stabilizers, and antioxidants, which are added in amounts effective to perform their intended function. Identification and use of these additives, and amounts thereof, is well within the skill of the art.

Suitable water softening agents include linear phosphates, styrene-maleic acid co-polymers, and polyacrylates. Suitable sequestrants include 1,3-dimethyl-2-immidazolidinone; 1-phenyl-3-isoheptyl-1,3-propanedione; and 2 hydroxy-5-nonylacetophenoneoxime.

Examples of corrosion inhibitors include zinc oxide, 2-aminomethyl propanol, diethylethanolamine benzotraizole, and methyl benzotriazole.

Examples of non-biological surface-active agents include polymers and surfactants, such as a quaternary ammonium surfactant, dodecyl benzene sulfonate, cetyltrimethylammonium bromide (CTAB), polyvinylpyrrolidone, fatty acid salts, sulfates, sulfonates, phosphoric surfactants, alkyl-ammoniums, alkyl-amines, fatty amine surfactants, alkyl ether sulfates, dodecyl benzene sulfonates, alpha olefin sulfonates, and/or amphoteric surfactants.

Examples of detergents include, for example, dodecyl benzene sulfonate, t-octylphenoxy-polyethoxyethanol, Triton X-100 or Tween 20. Examples of crystal modifiers include ethylene-vinyl acetate (EVA), polyethylene-butene (PEB), or polyethylene-propylene (PEP). Examples of stabilizers include glycol ester, propylene glycol, and ethylene glycol.

Examples of antioxidants suitable for the present invention include (BHT) 2,6-di-tert-butyl-para-cresol, (BHA) 2,6-di-tert-butyl-para-anisole, Eastman inhibitor O A B M-oxalyl bis (benzylidenehydrazide), and Eastman DTBMA 2,5-di-tert-butylhydroquinone.

In certain embodiments, the composition further comprises salts and/or mineral salts selected from sodium chloride, calcium chloride dihydrate, potassium chloride, magnesium chloride hexahydrate, phosphorous, magnesium, potassium, glucose and ammonium.

Other suitable additives, which may be contained in the formulations according to the invention, include substances that are customarily used for such preparations. The additives can be, for example, carriers, other microbe-based compositions produced at the same or different facility, viscosity modifiers, preservatives, tracking agents, poly(vinylpyrrolidone), methanol, butanol, biocides, driers, flow control agents, defoamers, UV stabilizers, anti-skinning agents, texturizers, emulsifying agents, lubricants, solubility controlling agents, and/or chelators.

In certain embodiments, the microbe cultures and/or growth byproducts thereof can replace traditional chemicals found in primers and other preparations. One example of a chemical that can be replaced by the microbe cultures and/or growth byproducts thereof is zinc oxide. Zinc oxide is often added to primers to minimize the leaching of a stain on a surface through the primer, as well as to reduce corrosion of metallic surfaces. Zinc cations react with an anionic stain to prevent leaching.

Advantageously, in accordance with the subject invention, the yeast-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Use of Microbes and their Growth Byproducts in Primers

In preferred embodiments, methods are provided for improving paint primers, wherein a SLP and/or a yeast culture comprising an SLP is added to the primer. In certain embodiments, the paint primer comprises one or more nanoparticle ingredients, such as pigments, UV-resisting agents, antimicrobials and/or anti-corrosion agents.

The use of primer compositions according to the subject invention can provide a variety of improvements upon application to a surface and/or object. The described elements of the subject invention are not an exhaustive examination of all applications.

In certain embodiments, the application of the microbe-containing and/or biosurfactant-containing composition to a primer may enhance the performance of the primer.

In certain embodiments, the microbe-containing and/or biosurfactant-containing primer can improve adhesion between the topcoat, such as, for example, paint, and the primer and/or between the primer and the surface to which the primer is applied. This improved adhesion can be established by creating a tie-coat layer, which is a transitional layer from the primer to the topcoat.

In certain embodiments, the microbe-containing and/or biosurfactant-containing primer can hide topographic variations of a surface and/or object to which it is applied. The variations can be physically altered by the application of the primer, whereby the primer can fill in depressions to level the surface. Alternatively, the primer can provide a visual illusion of a desired topography, with the physical variations remaining.

In certain embodiments, the microbe-containing and/or biosurfactant-containing primer can seal a porous object or surface. The object or surface can be sealed from penetration by gases, liquids, or solid substances. The sealing can make the object or surface waterproof, in which the no water can penetrate through the primer to reach the surface or object. Alternatively, the sealing can make the primer water-resistant, in which the primer can limit the amount of water that reaches the surface that would otherwise reach the surface if the primer was not applied.

In certain embodiments, the microbe-containing and/or biosurfactant-containing primer can stop color or stain bleeding. The origination of the stain can be, for example, cigarette smoke, grease, or tannins from certain types of wood. The color can be, for example, an existing dark paint color, scuff marks, pencil, marker, or crayon. The primer compositions of the subject invention can eliminate or reduce the penetration of the color or stain through the primer. As a result, fewer topcoats may be necessary. Additionally, required drying times of the primer and/or topcoat may be reduced.

In certain embodiments, the microbe-containing and/or biosurfactant-containing primer can stop odor dissemination from sources such as, for example, cigarette smoke, fire smoke, urine, and food. Certain embodiments of the subject invention can establish an airtight barrier between the surface that is coated by the primer and the surrounding environment.

In certain embodiments, the microbe-containing and/or biosurfactant-containing primer has increased longevity versus traditional primers due to its increased flexibility and resistance to cracking or blistering. Cracking or blistering is traditionally caused by physical forces on the primer, such as, for example, expansion or contraction of the surface to which the primer is applied. Additionally, the traditional chemical composition of a primer can, itself, promote cracking. Oil-based primers tend to be more likely to crack as the oils (e.g., fatty acids) in the primer continue to cross-link so long as the primer is exposed to oxygen. Thus, the subject invention provides primer compositions that can resist the cracking or blistering of oil-based primers.

In certain embodiments, the microbe-containing and/or biosurfactant-containing primer increases the longevity of a surface and/or object to which it is applied by preventing fouling of the surface and/or object by living organisms or non-living substances. The subject invention can be used to prevent deposition of organisms or precipitates. Thus, the present invention allows for delaying or completely removing the necessity for preventative maintenance related to removing precipitates and deposits, as well as the need for replacing or repairing equipment parts.

In certain embodiments, the biosurfactant in the primer improves the dispersion of nanoparticles that may be present in the composition. These can include pigments, as well as nanoparticles such as silicon dioxide, titanium dioxide, silver, zinc and others having, for example, antimicrobial, UV-reflecting. elasticity enhancing, or corrosion-preventing properties.

In some embodiments, the primer is a zinc rich primer comprising, for example, zinc oxide nanoparticles, wherein the biosurfactant enhances the dispersion of the zinc nanoparticles within the primer. Advantageously, when the zinc rich primer is applied to a surface, the zinc nanoparticles can be more uniformly spread over the surface to provide greater overall protection of the surface from corrosion.

The primer compositions of the subject invention can be applied to a variety of inorganic or organic objects such as, for example, steel, aluminum, wood, plastic, gypsum, paper, silk, glass, cotton, concrete, plaster, clay, stucco, plastic, rubber, hair, skin, fur, or plants. The compositions can be applied to objects that reside a range of temperatures, aquatic environments, or other stress-inducing conditions.

The composition can be applied to the surface by spraying using, for example, a spray bottle or a pressurized spraying device. The composition can also be applied using a cloth or a brush, wherein the composition is rubbed, spread or brushed onto the surface. Furthermore, the composition can be applied to the surface by dipping, dunking or submerging the surface into a container having the composition therein.

Oil and Gas Applications

In certain embodiments, the compositions of the subject invention can have applications in the oil and gas industry. For example, in some embodiments, applying a biosurfactant- and/or microbe-containing composition to a nanoparticle ingredient can produce an injection fluid for enhance oil and gas recovery from a hydrocarbon-bearing formation.

In certain embodiments, methods of enhancing oil recovery from a hydrocarbon-bearing formation are also provided, wherein the injection fluid is injected into a subterranean formation, followed by recovering the hydrocarbons.

In some embodiments, a biosurfactant and metallic nanoparticle composition (e.g., an aluminum can be useful for enhancing oil recovery from a formation, wherein the ionic properties of the nanoparticles force oil droplets out of the rock pores and the biosurfactants reduce the surface and interfacial tension within the formation, thereby providing a synergistic oil recovery mechanism.

In some embodiments, the nanoparticles are selected from the group consisting of aluminum, carbon, chromium, cobalt, copper, gold, iron, magnesium, nickel, platinum, silicon, silver, tin, titanium and zinc nanoparticles. In some embodiments, any of the nanoparticles described herein are metal oxide nanoparticles. In some embodiments, any of the nanoparticles described herein are mineral oxide nanoparticles. In some embodiments, the nanoparticles are aluminum oxide, antimony dioxide, copper oxide, iron oxide, magnesium oxide, nickel oxide, silicon dioxide, titanium oxide, zinc oxide, or zirconium dioxide nanoparticles.

In some embodiments, the nanoparticles are, for example, $Al_2O_3$, $Al(OH)_3$, $Bi_2O_3$, $CeO_2$, CoO, $CO_2O_3$, $CO_3O_4$, $Cr_2O_3$, CuO, $Cu_2O$, $Cu(OH)_2$, $Fe_2O_3$, $Fe_3O_4$, MgO, $Mg(OH)_2$, $MgCO_3$, $MnO_2$, $Mn_3O_4$, $Ni(OH)_2$, NiO, $SiO_2$. $SnO_2$, $TiO_2$, ZnO, $ZnCO_3$, $ZrO_2$, $Zr(OH)_4$, $BaCO_3$, $BaTiO_3$, $BaSO_4$, $CoFe_2O_4$, $CaCO_3$. $MnFe_2O_4$, $MgCO_3$, $ZnCO_3$, $SrCO_3$, $SrTiO_3$, $Cr_3C_2$, CrN, CdS, CuS, $Mg_3N_2$, $Mo_2C$, $MoS_2$, $MoSi_2$, NbC, SiC, $Si_3N_4$, and/or TiC.

In some embodiments, the composition can be used for removing deposits present in the subterranean formation. In some embodiments, the composition alters the wettability of the subterranean formation to be water wet. In some embodiments, the composition increases the relative permeability of the subterranean formation to hydrocarbons. In certain embodiments, the flow of hydrocarbons from the formation results from any of the above.

In some embodiments, the compositions described herein can be used to remediate subterranean formation depositions such as asphaltene, wax, scale, biofilms polymers and paraffin.

In some embodiments, the compositions can be used to improve the absolute permeability of fractured formation. In some embodiments, the compositions can be used to improve relative permeability to hydrocarbon.

The compositions described herein can also be used to increase the production of hydrocarbons from a subterranean formation that has already been subject to prior reservoir stimulation such as hydraulic fracturing or matrix stimulation.

In some embodiment, the nanoparticle ingredient comprises an enzyme encapsulated in, for example, polyethylenimine-dextran sulfate or other polymers, which can, for example, digest guar gum or other cross-linked fracking polymers that buildup in a formation.

In some embodiments, the nanoparticle is a nano-proppant, which can be injected into a formation to prop nanoscale fractures produced by hydraulic fracturing. Preferably, the nano-proppant comprises mechanical properties such as stiffness (resistance to deformation) and strength under compressive loads (resistance to crush), combined with sufficient toughness to avoid the brittle fracture of the particles into small pieces commonly known as fines. In addition, the particles must have excellent heat resistance to be able to withstand the combination of high compressive load and high temperature that normally becomes increasingly more severe as one drills deeper. The good transport and low settling ability of proppants is another feature that has to be considered when choosing the propping agent. In some embodiments, the nano-proppant comprises, for example, carbon black, carbon nanotubes and nanofibers, fumed silica and alumina and/or cellulosic nanofibers, nanoclays and finely divided grades of fly ash.

In some embodiments, the composition described herein may be used in thermal oil recovery as an additive to hot water/steam which may improve the interfacial properties between injected aqueous phase and heavy oil in place, which may lead to increased performance and/or higher recovery. In some embodiments, the composition described herein may be used to potentially enhance bitumen extraction. Specifically, the composition described herein may be added as an additive in the hot water which may improve bitumen separation from sand particles by potentially reducing the interfacial tension between bitumen droplets and water.

In some embodiments, the composition described herein may be used for water treatment. Specifically, the composition described herein may be added to water which may cause separation of certain impurities (organic and inorganic residues) through enhancing aggregation of such impurities and their segregation by nanoparticles. In some embodiments, the composition could be used for injection into salt water disposal wells. Specifically, the composition described herein could be injected into salt water disposal wells to help remove and/or loosen the buildup of organic material. The increased buildup in the well makes it necessary to use a higher injection pressure, which can be significantly reduced with treatment.

Agriculture Applications

In certain embodiments, the compositions of the subject invention can be used for agricultural applications. Because many organic functions such as ion exchange and plant gene expression operate on small scales, nanomaterials, such as nanofertilizers and nanopesticides, offer a toolset that works at the right scale to provide efficient, targeted delivery to living cells. Environmentally-conscious nanofertilizers can provide efficient ion and nutrient delivery into plant cells. See Miranda-Villagomez et al. 2019, incorporated herein by reference in its entirety.

In certain embodiments, methods for producing an improved fertilizer composition are provided, comprising applying the biosurfactant composition to a nanoparticle ingredient, wherein the nanoparticle ingredient is a nanofertilizer component. Nanofertilizers can comprise, for example, nanoscale fertilizers (nanoparticles that contain nutrients), nanoscale additives (traditional fertilizers with nanoscale additives) and nanoscale coatings (traditional fertilizers coated or loaded with nanoparticles). In some embodiments, the nanoparticle ingredient is a nanoparticle containing one or more nutrients, such as, for example, carbon (C), hydrogen (H), oxygen (O), nitrogen (N), phosphorus (P), potassium (K), sulfur (S), calcium (Ca). magnesium (Mg), boron (B), chlorine (Cl), copper (Cu), iron (Fe), manganese (Mn), molybdenum (Mo), nickel (Ni), and zinc (Zn). In certain embodiment, a nanoparticle loaded with the one or more nutrients is utilized, for example, a chitosan, polyacrylamide, polyacrylate, or zeolite nanoparticle.

Advantageously, through application of a biosurfactant and/or microbe-based composition according to the subject invention in combination with the nanoparticle ingredient(s), the subject invention can enhance dispersion of nutrients within soil and enhance nutrient availability and absorption by plant roots compared with the application of nanoparticle ingredient(s) (e.g., nanofertilizers) without the biosurfactant and/or microbe-based composition.

Healthcare Applications

In certain embodiments, the compositions of the subject invention can be used for human health applications, for example, as a delivery aid and for transporting materials across the blood-brain barrier (BBB).

In certain embodiments, the subject invention provides methods for producing an improved healthcare composition, comprising applying a biosurfactant to a nanoparticle ingredient, wherein the nanoparticle ingredient is, for example, a liposome-based nanoparticle, metal nanoparticle (e.g., gold nanoparticle), polymeric nanoparticle, ionorganic nanoparticle, viral nanoparticle, lipid-based nanoparticle, or nanoparticle albumin-bound technology comprising and/or encapsulating a health-promoting compound. The health-promoting compound can be, for example, a pharmaceutical, an over-the-counter drug, a nutraceutical, a supplement, a vitamin and/or a mineral.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Uses of Nanoparticles

Provided are examples of nanoparticle (NP) applications for which the subject invention can be used to produce and/or enhance nanoparticle compositions Electrons/Magnets
- Magnetic nanoparticles used to replace radioactive technetium for tracking the spread of cancer
- Valuable for use in batteries and supercapacitors.
- Blue LEDS
- Replace radioactive technetium, for tracking the spread of cancer along lymph nodes Imaging
- Enhance florescent imaging
- Enhance images for PET/Ultrasound
- Gold NP used for SEM
- photocatalysis, photo optics and electronic devices Biomaterials
- Scaffold structure for tissue/bone repair
- Can enter cells or be designed to bind to specific cells
  - Facilitated development of new, methods of delivering therapy—blocking vasculature to diseased tissues
- Drugs carried vis nanocapsule(liposome) or porous nanosponge structures
- Delivery of drug to brain via inhalation
- Synthesis of lipid NPs for various applications such as drug carriers and delivery and RNA release in cancer
- Chemotherapy drugs attached to nanodiamonds are being tested for brain tumor treatment
- Gold nanoparticles are extensively used in immunohistochemistry to detect the interaction between proteins.
- Blood-triggered generation of platinum nanoparticle functions as an anti-cancer agent Ceramics/ART
- Nanoclays-incorporated into polymers to improve their strength and impact resistance Environment
- Nanoparticles are used extensively in sculptures and painting
- Zero-valent iron (NZVI) particles as a field-deployable means of remediating organochlorine compounds—PCBs
- Copper tungsten oxide nanoparticles to break down oil into biodegradable compounds
- Permeate in rock layers—neutralize reactivity of organochlorines in aquifers Manufacturing
- Increasingly incorporated into food packaging
- Antimicrobial effects-nanocopper or nanosilver packaging
- Health related products
- Antiviral
- Antifungal Chemistry
- Replace additives based on flammable organic halogens and phosphorus in plastics and textiles
- Catalysis
- Photodegradation of dyes Use in Drug Delivery
- Nanosuspension and nanocrystals—Drug power is dispersed in surfactant solution
- Solid lipid nanoparticles—Melting lipid dispersed in aqueous surfactant—less toxic and more stable colloidal carrier systems as alternative materials to polymers
- Polymeric nanoparticles—Biodegradable polymers—controlled and targeted drug delivery
- Polymeric micelles
- Magnetic Nanoparticles
- Carbon nanotubes
- Liposomes—phospholipid vesicles
- Nanoshells
- Ceramics—Silica, alumina, titania (drug biomolecule)
- Nanopores
- Nano wires
- Quantum, dots
- Nano films
- Ferrofluids

Example 2—Additional Exemplary Uses of Nanoparticles

Provided are additional examples of nanoparticle (NP) applications for which the subject invention can be used to produce and/or enhance nanoparticle compositions.
- Nanoscale additives to or surface treatments of fabrics can provide lightweight ballistic energy deflection in personal body armor, or can help them resist wrinkling, staining, and bacterial growth.

- Clear nanoscale films on eyeglasses, computer and camera displays, windows, and other surfaces can make them water- and residue-repellent, antireflective, self-cleaning, resistant to ultraviolet or infrared light, antifog, antimicrobial, scratch-resistant, or electrically conductive.
- Nanoscale materials are beginning to enable washable, durable "smart fabrics" equipped with flexible nanoscale sensors and electronics with capabilities for health monitoring, solar energy capture, and energy harvesting through movement.
- Lightweighting of cars, trucks, airplanes, boats, and space craft could lead to significant fuel savings. Nanoscale additives in polymer composite materials are being used in baseball bats, tennis rackets, bicycles, motorcycle helmets, automobile parts, luggage, and power tool housings, making them lightweight, stiff, durable, and resilient. Carbon nanotube sheets are now being produced for use in next-generation air vehicles. For example, the combination of light weight and conductivity makes them ideal for applications such as electromagnetic shielding and thermal management.
- Nano-bioengineering of enzymes is aiming to enable conversion of cellulose from wood chips, corn stalks, unfertilized perennial grasses, etc., into ethanol for fuel. Cellulosic nanomaterials have demonstrated potential applications in a wide array of industrial sectors, including electronics, construction, packaging, food, energy, health care, automotive, and defense. Cellulosic nanomaterials are projected to be less expensive than many other nanomaterials and, among other characteristics, tout an impressive strength-to-weight ratio.
- Nano-engineered materials in automotive products include high-power rechargeable battery systems; thermoelectric materials for temperature control; tires with lower rolling resistance; high-efficiency/low-cost sensors and electronics; thin-film smart solar panels; and fuel additives for cleaner exhaust and extended range.
- Nanostructured ceramic coatings exhibit much greater toughness than conventional wear-resistant coatings for machine parts. Nanotechnology-enabled lubricants and engine oils also significantly reduce wear and tear, which can significantly extend the lifetimes of moving parts in everything from power tools to industrial machinery.
- Nanoparticles are used increasingly in catalysis to boost chemical reactions. This reduces the quantity of catalytic materials necessary to produce desired results, saving money and reducing pollutants. Two big applications are in petroleum refining and in automotive catalytic converters.
- Nano-engineered materials make superior household products such as degreasers and stain removers; environmental sensors, air purifiers, and filters; antibacterial cleansers; and specialized paints and sealing products, such a self-cleaning house paints that resist dirt and marks.
- Nanoscale materials are also being incorporated into a variety of personal care products to improve performance. Nanoscale titanium dioxide and zinc oxide have been used for years in sunscreen to provide protection from the sun while appearing invisible on the skin.

Electronics and IT Applications

Nanotechnology has greatly contributed to major advances in computing and electronics, leading to faster, smaller, and more portable systems that can manage and store larger and larger amounts of information. These continuously evolving applications include:

- Transistors, the basic switches that enable all modern computing, have gotten smaller and smaller through nanotechnology. At the turn of the century, a typical transistor was 130 to 250 nanometers in size. In 2014, Intel created a 14 nanometer transistor, then IBM created the first seven nanometer transistor in 2015, and then Lawrence Berkeley National Lab demonstrated a one nanometer transistor in 2016! Smaller, faster, and better transistors may mean that soon your computer's entire memory may be stored on a single tiny chip.
- Using magnetic random access memory (MRAM), computers will be able to "boot" almost instantly. MRAM is enabled by nanometer-scale magnetic tunnel junctions and can quickly and effectively save data during a system shutdown or enable resume-play features.
- Ultra-high definition displays and televisions are now being sold that use quantum dots to produce more vibrant colors white being more energy efficient.
- Flexible, bendable, foldable, rollable, and stretchable electronics are reaching into various sectors and are being integrated into a variety of products, including wearables, medical applications, aerospace applications, and the Internet of Things. Flexible electronics have been developed using, for example, semiconductor nanomembranes for applications in smartphone and e-reader displays. Other nanomaterials like graphene and cellulosic nanomaterials are being used for various types of flexible electronics to enable wearable and "tattoo" sensors, photovoltaics that can be sewn onto clothing, and electronic paper that can be rolled up. Making flat, flexible, lightweight, non-brittle, highly efficient electronics opens the door to countless smart products.
- Other computing and electronic products include Flash memory chips for smart phones and thumb drives; ultra-responsive hearing aids; antimicrobial/antibacterial coatings on keyboards and cell phone casings; conductive inks for printed electronics for RFID/smart cards/smart packaging; and flexible displays for e-book readers.
- Nanoparticle copper suspensions have been developed as a safer, cheaper, and more reliable alternative to lead-based solder and other hazardous materials commonly used to fuse electronics in the assembly process.

Medical and Healthcare Applications

Nanotechnology is already broadening the medical tools, knowledge, and therapies currently available to clinicians. Nanomedicine, the application of nanotechnology in medicine, draws on the natural scale of biological phenomena to produce precise solutions for disease prevention, diagnosis, and treatment. Below are some examples of recent advances in this area:

- Commercial applications have adapted gold nanoparticles as probes for the detection of targeted sequences of nucleic acids, and gold nanoparticles are also being clinically investigated as potential treatments for cancer and other diseases.
- Better imaging and diagnostic tools enabled by nanotechnology are paving the way for earlier diagnosis, more individualized treatment options, and better therapeutic success rates.
- Nanotechnology is being studied for both the diagnosis and treatment of atherosclerosis, or the buildup of plaque in arteries. In one technique, researchers created a nanoparticle that mimics the body's "good" cholesterol, known as HDL (high-density lipoprotein), which helps to shrink plaque.

The design and engineering of advanced solid-state nanopore materials could allow for the development of novel gene sequencing technologies that enable single-molecule detection at low cost and high speed with minimal sample preparation and instrumentation.

Nanotechnology researchers are working on a number of different therapeutics where a nanoparticle can encapsulate or otherwise help to deliver medication directly to cancer cells and minimize the risk of damage to healthy tissue. This has the potential to change the way doctors treat cancer and dramatically reduce the toxic effects of chemotherapy.

Research in the use of nanotechnology for regenerative medicine spans several application areas, including bone and neural tissue engineering. For instance, novel materials can be engineered to mimic the crystal mineral structure of human bone or used as a restorative resin for dental applications. Researchers are looking for ways to grow complex tissues with the goal of one day growing human organs for transplant. Researchers are also studying ways to use graphene nanoribbons to help repair spinal cord injuries; preliminary research shows that neurons grow well on the conductive graphene surface.

Nanomedicine researchers are looking at ways that nanotechnology can improve vaccines, including vaccine delivery without the use of needles. Researchers also are working to create a universal vaccine scaffold for the annual flu vaccine that would cover more strains and require fewer resources to develop each year.

Energy Applications

Nanotechnology is finding application in traditional energy sources and is greatly enhancing alternative energy approaches to help meet the world's increasing energy demands. Many scientists are looking into ways to develop clean, affordable, and renewable energy sources, along with means to reduce energy consumption and lessen toxicity burdens on the environment:

Nanotechnology is improving the efficiency of fuel production from raw petroleum materials through better catalysis. It is also enabling reduced fuel consumption in vehicles and power plants through higher-efficiency combustion and decreased friction.

Nanotechnology is also being applied to oil and gas extraction through, for example, the use of nanotechnology-enabled gas lift valves in offshore operations or the use of nanoparticles to detect microscopic down-well oil pipeline fractures.

Researchers are investigating carbon nanotube "scrubbers" and membranes to separate carbon dioxide from power plant exhaust.

Researchers are developing wires containing carbon nanotubes that will have much lower resistance than the high-tension wires currently used in the electric grid, thus reducing transmission power loss.

Nanotechnology can be incorporated into solar panels to convert sunlight to electricity more efficiently, promising inexpensive solar power in the future. Nanostructured solar cells could be cheaper to manufacture and easier to install, since they can use print-like manufacturing processes and can be made in flexible rolls rather than discrete panels. Newer research suggests that future solar converters might even be "palatable."

Nanotechnology is already being used to develop many new kinds of batteries that are quicker-charging, more efficient, lighter weight, have a higher power density, and hold electrical charge longer.

An epoxy containing carbon nanotubes is being used to make windmill blades that are longer, stronger, and lighter-weight than other blades to increase the amount of electricity that windmills can generate.

In the area of energy harvesting, researchers are developing thin-film solar electric panels that can be fitted onto computer cases and flexible piezoelectric nanowires woven into clothing to generate usable energy on the go from light, friction, and/or body heat to power mobile electronic devices. Similarly, various nanoscience-based options are being pursued to convert waste heat in computers, automobiles, homes, power plants, etc., to usable electrical power.

Energy efficiency and energy saving products are increasing in number and types of application. In addition to those noted above, nanotechnology is enabling more efficient lighting systems; lighter and stronger vehicle chassis materials for the transportation sector; lower energy consumption in advanced electronics; and light-responsive smart coatings for glass.

Environmental Remediation

In addition to the ways that nanotechnology can help improve energy efficiency (see the section above), there are also many ways that it can help detect and clean up environmental contaminants:

Nanotechnology could help meet the need for affordable, clean drinking water through rapid, low-cost detection and treatment of impurities in water.

Engineers have developed a thin film membrane with nanopores for energy-efficient desalination. This molybdenum disulphide ($MoS_2$) membrane filtered two to five times more water than current conventional filters.

Nanoparticles are being developed to clean industrial water pollutants in ground water through chemical reactions that render the pollutants harmless. This process would cost less than methods that require pumping the water out of the ground for treatment.

Researchers have developed a nanofabric "paper towel" woven from tiny wires of potassium manganese oxide that can absorb 20 times its weight in oil for cleanup applications. Researchers have also placed magnetic water-repellent nanoparticles in oil spills and used magnets to mechanically remove the oil from the water.

Many airplane cabin and other types of air filters are nanotechnology-based filters that allow "mechanical filtration," in which the fiber material creates nanoscale pores that trap particles larger than the size of the pores. The filters also may contain charcoal layers that remove odors.

Nanotechnology-enabled sensors and solutions are now able to detect and identify chemical or biological agents in the air and soil with much higher sensitivity than ever before. Researchers are investigating particles such as self-assembled monolayers on mesoporous supports (SAMMS™), dendrimers, and carbon nanotubes to determine how to apply their unique chemical and physical properties for various kinds of toxic site remediation. Another sensor has been developed by NASA as a smartphone extension that firefighters can use to monitor air quality around fires.

Future Transportation Benefits

Nanotechnology offers the promise of developing multi-functional materials that will contribute to building and maintaining lighter, safer, smarter, and more efficient vehicles, aircraft, spacecraft, and ships. In addition, nanotechnology offers various means to improve the transportation infrastructure:

As discussed above, nano-engineered materials in automotive products include polymer nanocomposites structural parts; high-power rechargeable battery systems; thermoelectric materials for temperature control; lower rolling-resistance tires; high-efficiency/low-cost sensors and electronics; thin-film smart solar panels; and fuel additives and improved catalytic converters for cleaner exhaust and extended range. Nano-engineering of aluminum, steel, asphalt, concrete and other cementitious materials, and their recycled forms offers great promise in terms of improving the performance, resiliency, and longevity of highway and transportation infrastructure components while reducing their life cycle cost. New systems may incorporate innovative capabilities into traditional infrastructure materials, such as self-repairing structures or the ability to generate or transmit energy.

Nanoscale sensors and devices may provide cost-effective continuous monitoring of the structural integrity and performance of bridges, tunnels, rails, parking structures, and pavements over time. Nanoscale sensors, communications devices, and other innovations enabled by nanoelectronics can also support an enhanced transportation infrastructure that can communicate with vehicle-based systems to help drivers maintain lane position, avoid collisions, adjust travel routes to avoid congestion, and improve drivers' interfaces to onboard electronics.

"Game changing" benefits from the use of nanotechnology-enabled lightweight, high-strength materials would apply to almost any transportation vehicle. For example, it has been estimated that reducing the weight of a commercial jet aircraft by 20 percent could reduce its fuel consumption by as much as 15 percent. A preliminary analysis performed for NASA has indicated that the development and use of advanced nanomaterials with twice the strength of conventional composites would reduce the gross weight of a launch vehicle by as much as 63 percent. Not only could this save a significant amount of energy needed to launch spacecraft into orbit, but it would also enable the development of single stage to orbit launch vehicles, further reducing launch costs, increasing mission reliability, and opening the door to alternative propulsion concepts.

Example 3—Primer with Acidic or Lactonic SLP Blocks Stain Bleeding

Figure 2:
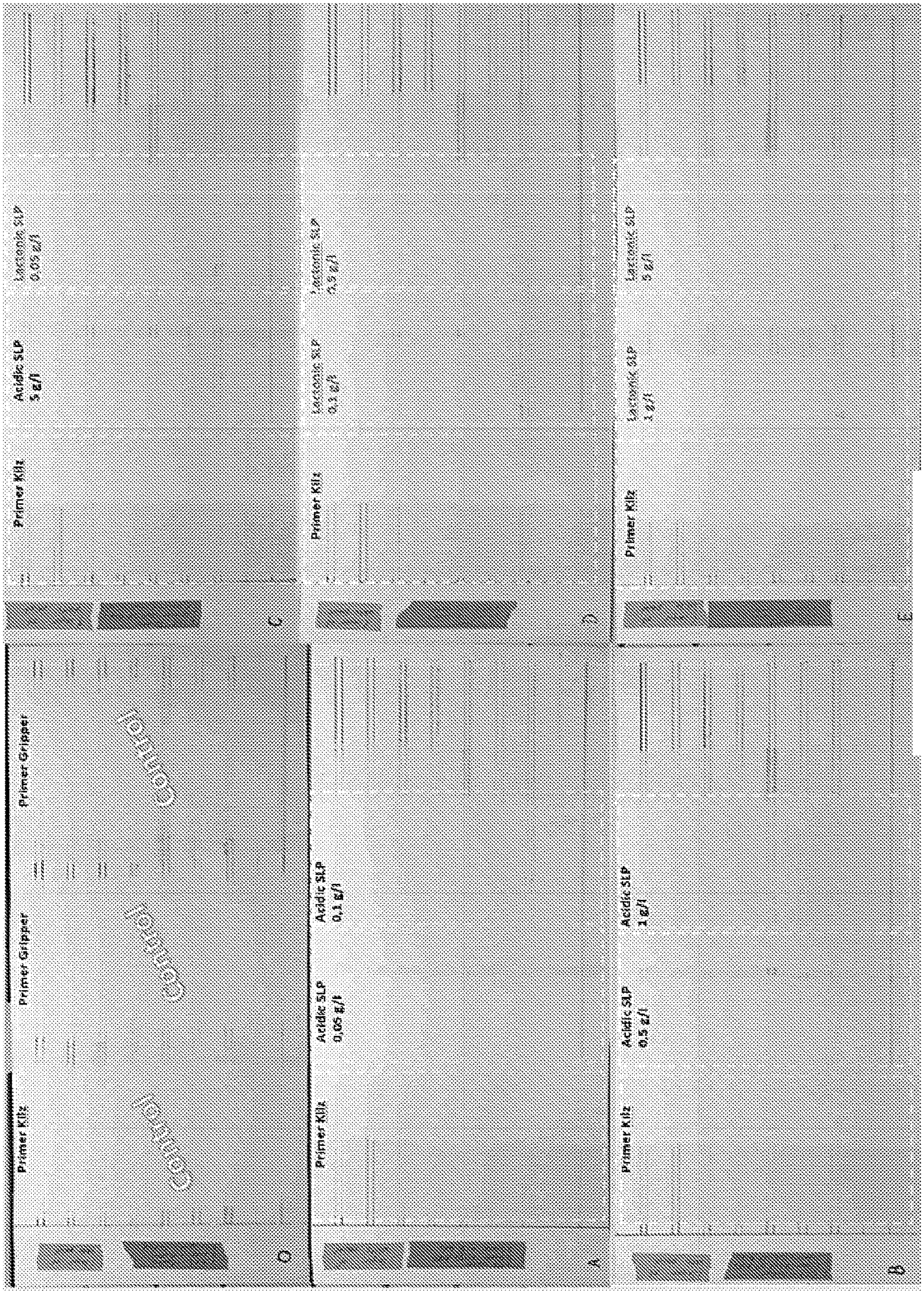
FIG. 2 shows six testing panels of a Leneta drawdown chart. Control testing panel (#0) was painted with a single layer of Kilz primer in the left column, and a single layer of the Gripper primer was applied to the center and right columns. In the left column of Panels A, B, C, D, and E, one layer of Kilz primer was applied. In the center and right columns of Panels A, B, C, D, and E, one layer of Gripper primer mixed with 0.05 g/l, 0.1 g/l, 0.5 g/l, 1 g/l, or 5 g/l of either acidic or lactonic SLP was applied. Panel A shows 0.05 g/l of acidic SLP and 0.1 g/l of acidic SLP, panel B shows 0.5 g/l of acidic SLP and 1 g/l of acidic SLP, panel C demonstrates 5 g/l of acidic SLP and 0.05 g/l of lactonic SLP, panel D shows 0.1 g/l of lactonic SLP and 0.5 g/l of lactonic SLP, and panel E demonstrates 1 g/l of lactonic SLP and 5 g/l of lactonic SLP. Then, after drying overnight, a narrower drawdown application of a single layer of the premium paint was applied over the primer layer in each of the three columns, resulting in the drawdown charts of FIG. 2.

A Leneta drawdown paperboard chart was used to evaluate the ability of paint primers with added SLP to block stains. Initially, the drawdown chart was painted with a premium flat paint using a drawdown applicator. To test the ability of primers to block stains, a variety of hydrophobic and hydrophilic writing implements were applied to a one-week-old dried premium flat paint. The markers include: black Sharpie®, red Sharpie®, blue Paper Mate®, orange Paper Mate®, black pen, red pen, blue pen, pink washable marker, and blue washable marker (FIG. 1). Primers were applied by drawdown bar across the marker lines on the chart. In the left column of Panels A, B, C, D, and E, one layer of Kilz primer was applied. In the center and right columns of Panels A, B, C, D, and E, one layer of Gripper primer mixed with 0.05 g/l, 0.1 g/l, 0.5 g/l, 1 g/l, or 5 g/l of either acidic or lactonic SLP was applied. Panel A shows 0.05 g/l of acidic SLP and 0.1 g/l of acidic SLP, panel B shows 0.5 g/l of acidic SLP and 1 g/l of acidic SLP, panel C demonstrates 5 g/l of acidic SLP and 0.05 g/l of lactonic SLP, panel D shows 0.1 g/l of lactonic SLP and 0.5 g/l of lactonic SLP, and panel E demonstrates 1 g/l of lactonic SLP and 5 g/l of lactonic SLP. Control testing panel (#0) was painted with a single layer of Kilz primer in the left column, and a single layer of the Gripper primer was applied to the center and right columns. After drying overnight, a narrower drawdown of the premium, flat, white paint was applied over the primer (FIG. 2).

Figure 3:
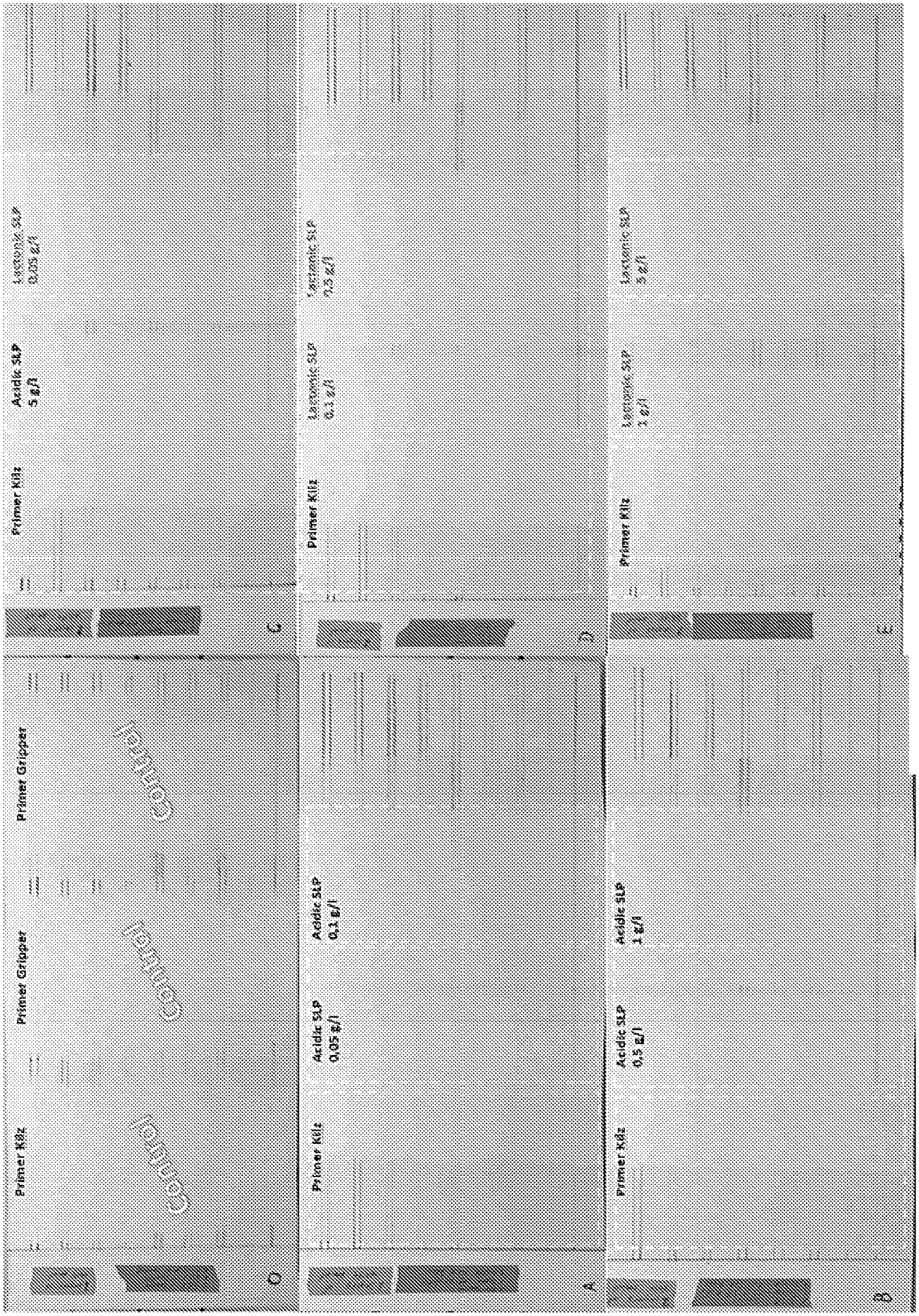
FIG. 3 shows six testing panels of a Leneta drawdown chart, corresponding to the application of an additional layer of premium paint (two total layers) over the initial primer layer and the single layer of paint that were applied previously (shown in FIG. 2).

Finally, an even narrower-width of a second coat of the premium, flat, white paint was applied across each column using a drawdown applicator (FIG. 3).

Paint and primer with SLP covers the writing implement stains better that paint and primer without SLP. Better coverage of the stains was observed with the primers containing acidic SLP in the lower (0.05 g/l and 0.1 g/l) concentrations. Adding acidic or lactonic SLP in concentrations of 0.05 g/l or 0.1 g/l to the primer allowed for full coverage of all hydrophobic markers and almost all hydrophilic markers. Additionally, primers with added SLP are more flexible than primers without SLP. Adding SLP to water-based primers creates an environmentally friendly, safe and easy to use product.

Example 4—Primer with Acidic or Lactonic SLP Blocks Color Bleeding

Figure 4:
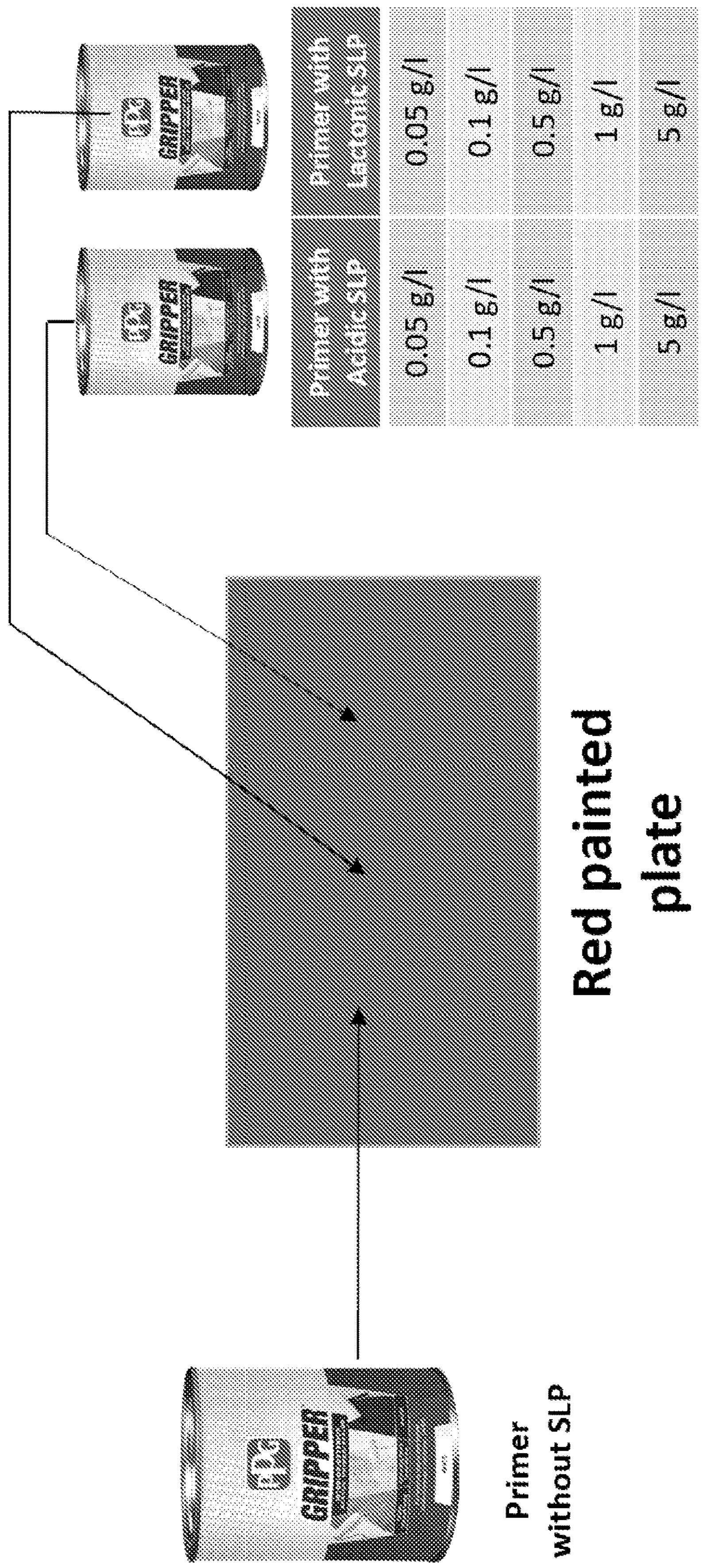
FIG. 4 shows a red-painted drywall plate used to investigate paint color bleeding. Gripper primer without SLP, Gripper primer with 5 different concentrations with acidic SLP, and Gripper primer with 5 different concentrations of lactonic SLP were applied to the drywall. Additionally, semi-gloss interior paint can be applied on top of the various primer compositions.
Figure 5A:
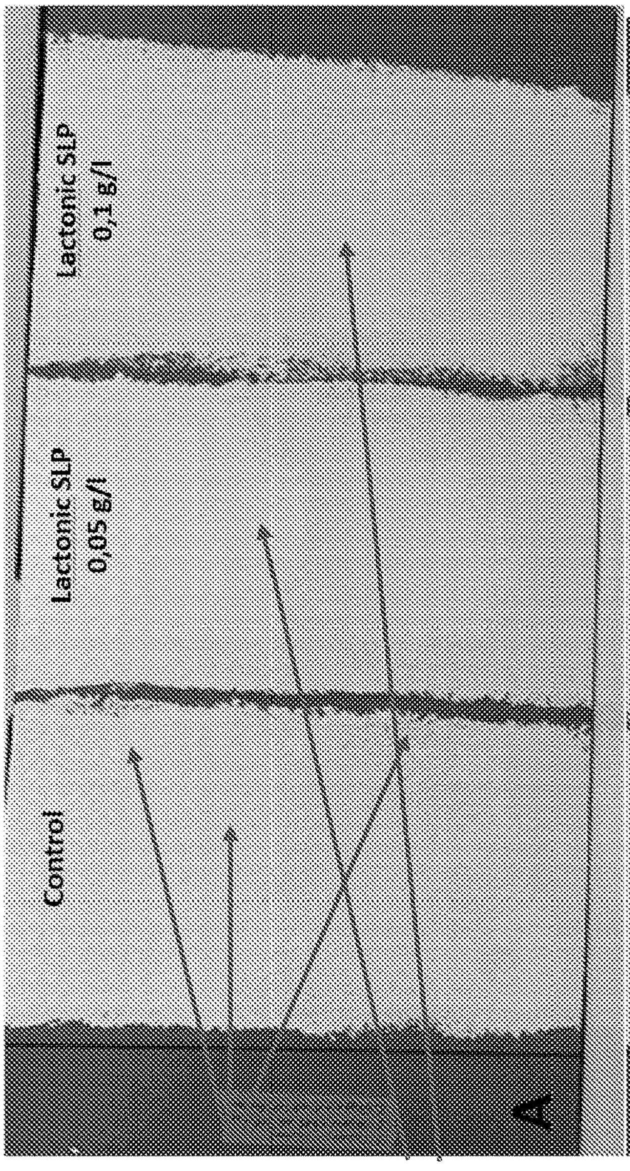
FIGS. 5A-5E show the plates, as described in the description of FIG. 4 with the various primer compositions applied.
Figure 5B:
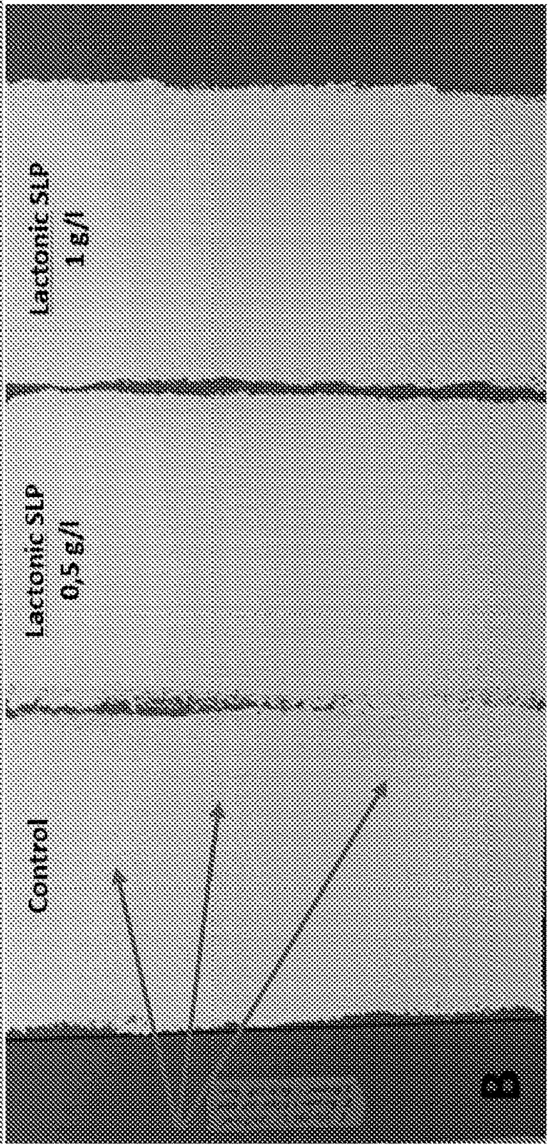
Figure 5C:
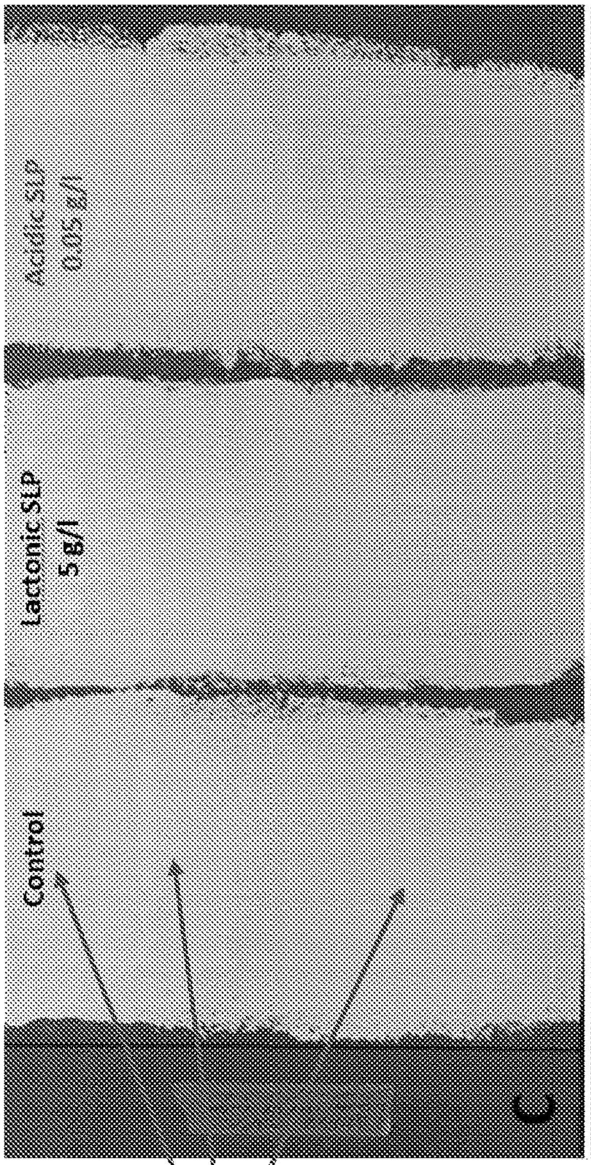
Figure 5D:
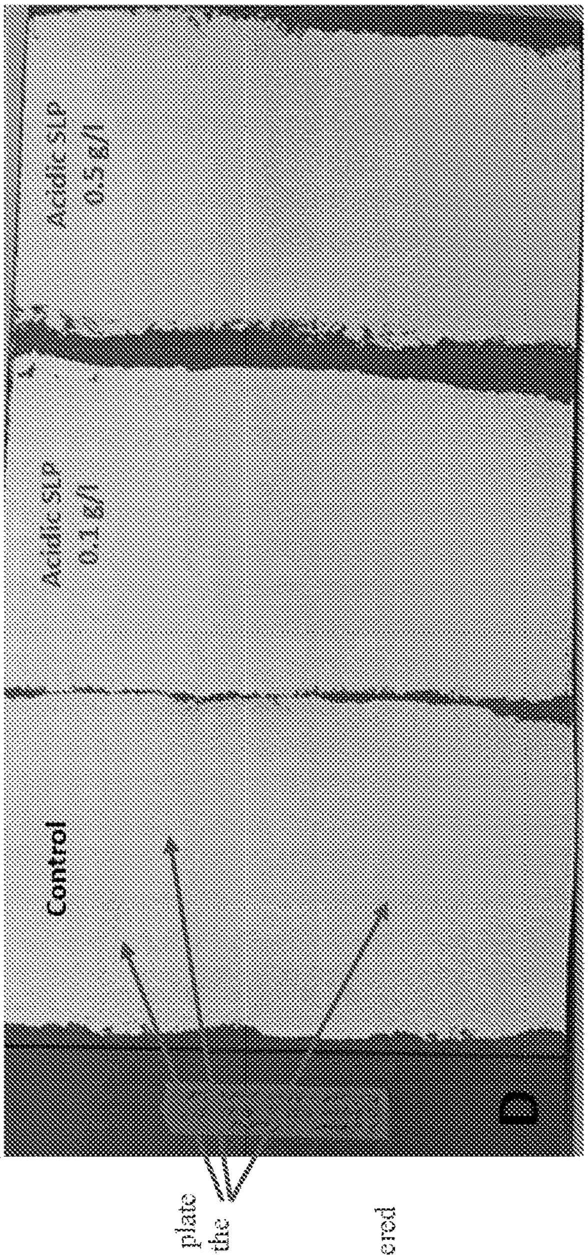
Figure 5E:
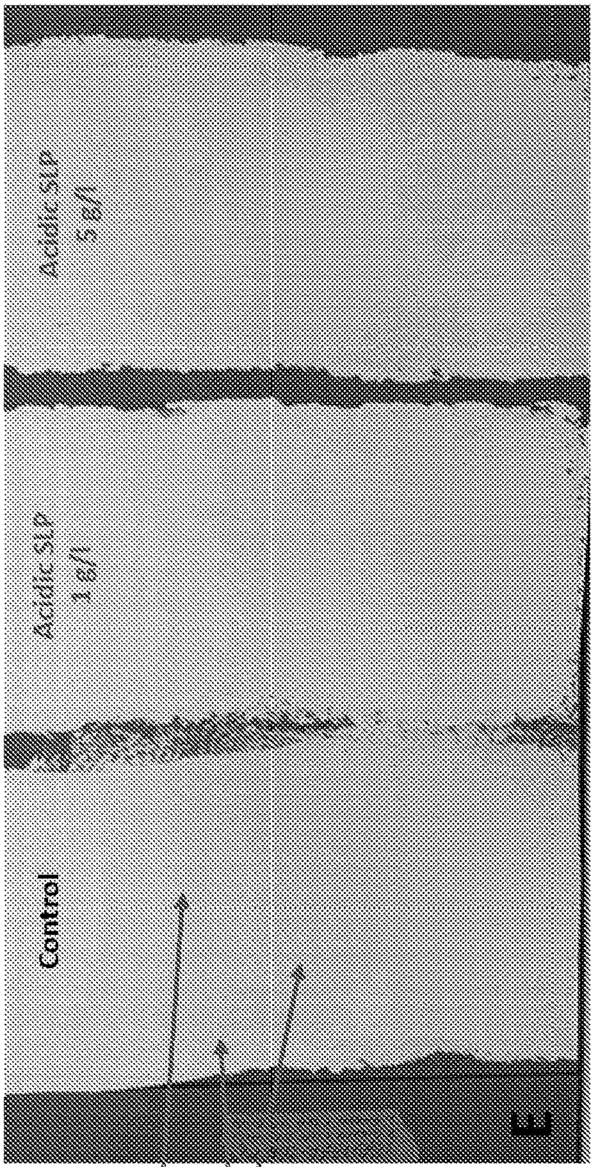

Red painted drywall panels with dimensions of 2 ft by 1 ft. were used to evaluate the ability of paint primers with SLPs to reduce color bleeding. Primers are applied by drawdown bar to dried premium red flat painted drywall panels (FIG. 4). Either acidic or lactonic SLPs at concentration of 0.05 g/L, 0.1 g/L, 0.5 g/L, 1 g/L, or 5 g/L are added to a water-based (Gripper) primer and applied to the red painted drywall panels (FIG. 5). The left column is the control (Gripper primer without added SLP). The center and right columns illustrate Gripper primer with various concentrations of acidic or lactonic SLPs. FIG. 5A shows primers with 0.05 g/l of lactonic SLP or 0.1 g/l of lactonic SLP; FIG. 5B shows primers with 0.5 g/l of lactonic SLP and 1 g/l of lactonic SLP; FIG. 5C shows primers with 5 g/l of lactonic SLP or 0.05 g/l of acidic SLP; FIG. 5D shows primers with 0.1 g/l of acidic SLP or 0.5 g/l of acidic SLP; and FIG. 5E shows primers with 1 g/l of acidic SLP or 5 g/l of acidic SLP.

Figure 6A:
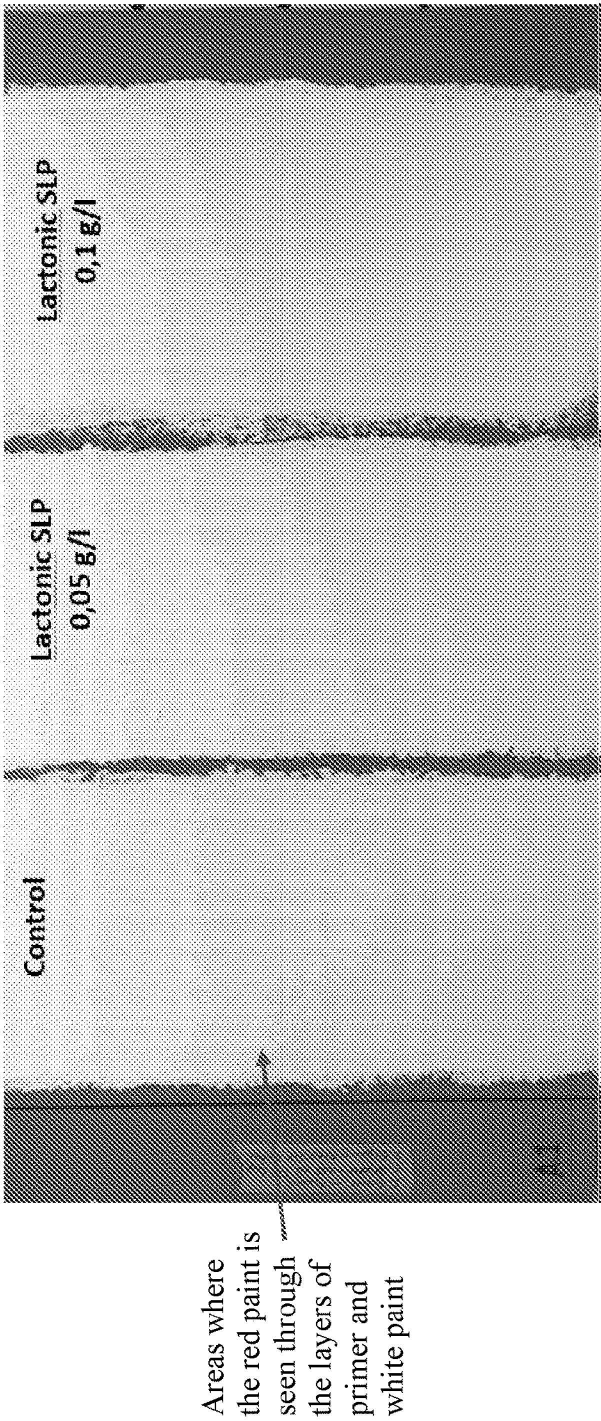
FIGS. 6A-6E show the next step after the primers were in applied in FIGS. 5A-5E, wherein a layer of premium interior white paint was applied to the dried primer layer.
Figure 6B:
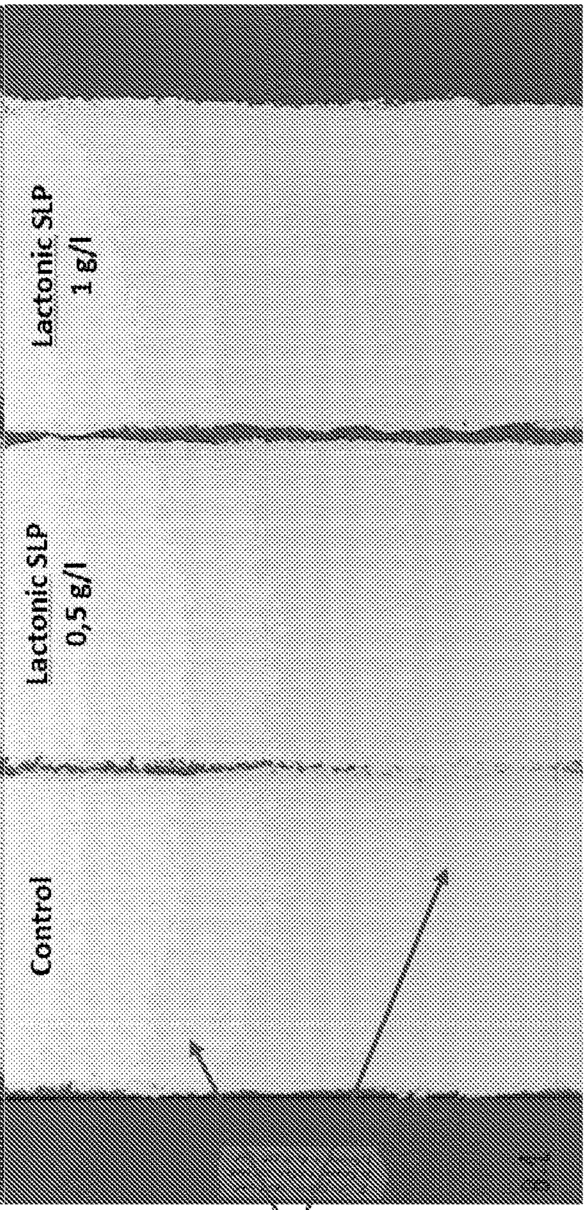
Figure 6C:
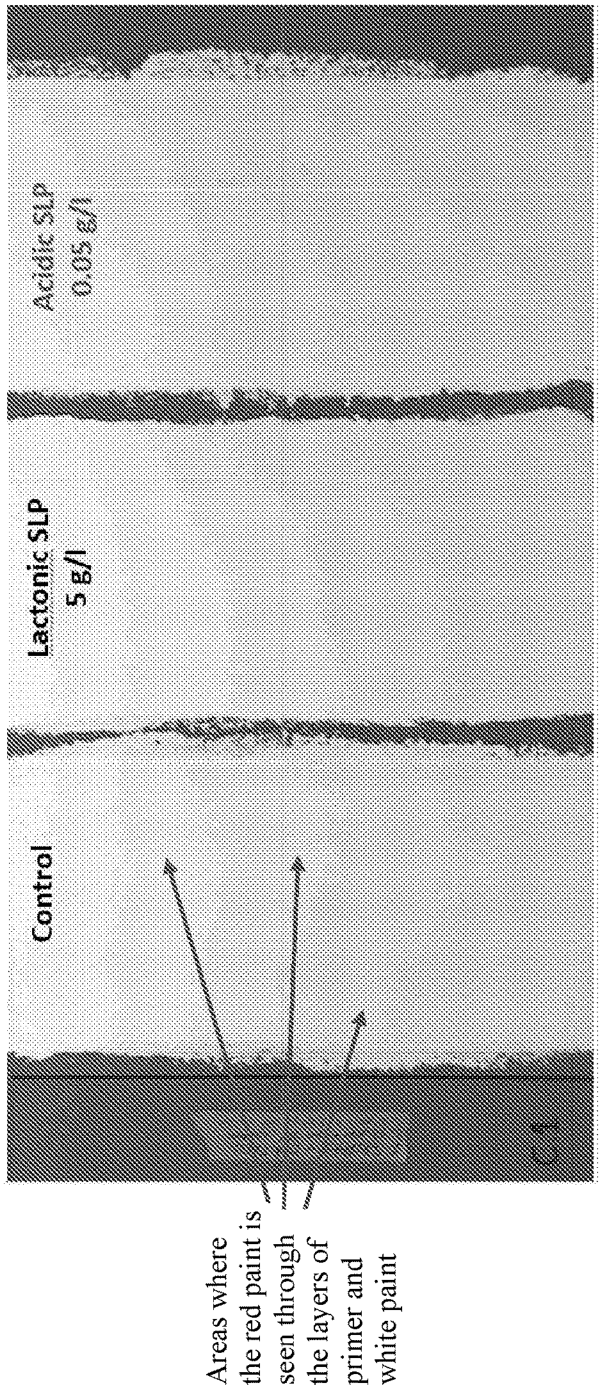
Figure 6D:
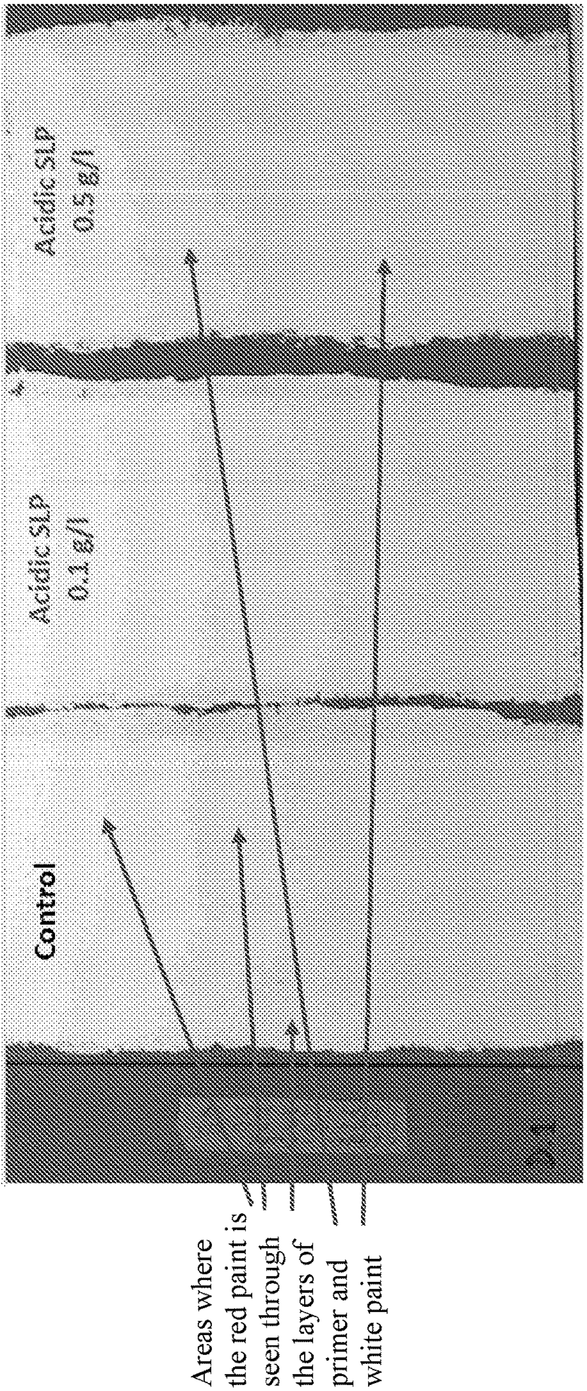
Figure 6E:
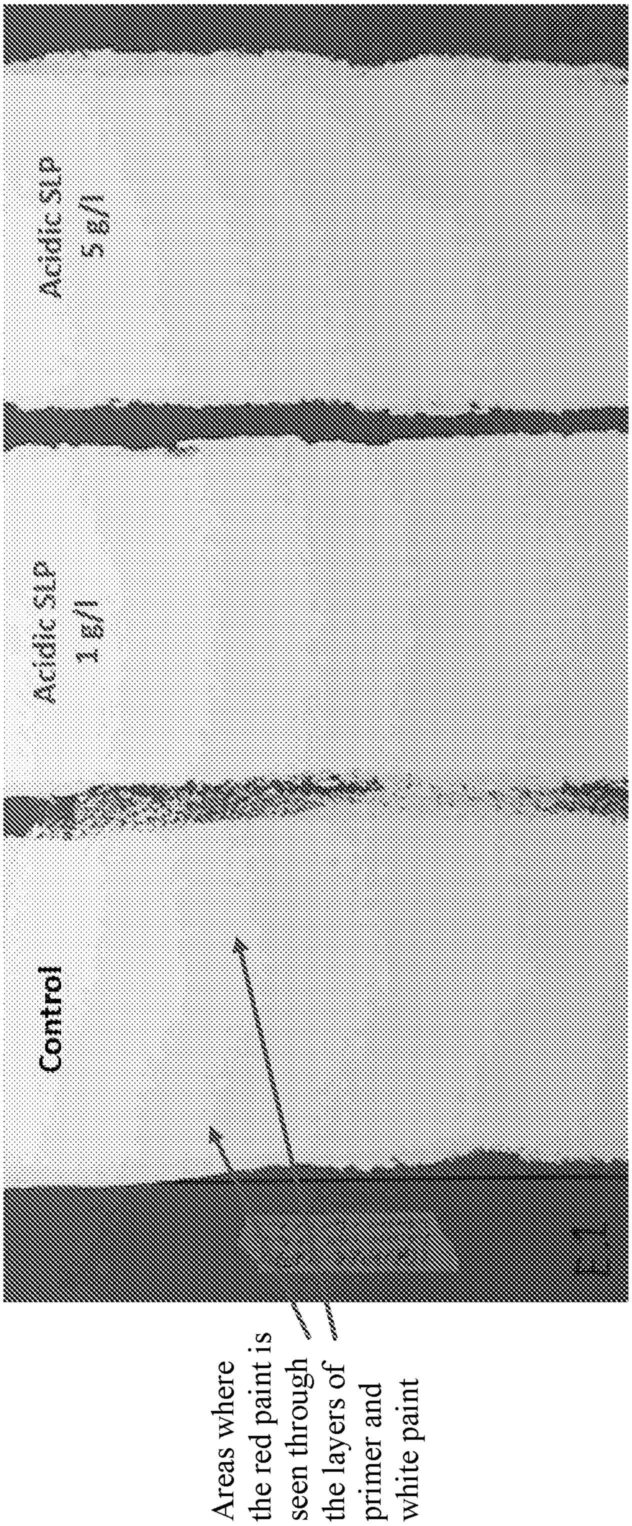

In a second stage of testing, after the primer layer dries overnight, a narrower drawdown of semi-gloss interior white paint was applied over the dried primer layers. FIGS. 6A-6E illustrate the white painted drywall panels. FIG. 6A shows the layer of white paint over the layer of primer with 0.05 g/l of lactonic SLP or 0.1 g/l of lactonic SLP; FIG. 6B shows the layer of white paint over the layer of primer with 0.5 g/l of lactonic SLP or 1 g/l of lactonic SLP; FIG. 6C s shows the layer of white paint over the layer of primer with 5 g/l of lactonic SLP or 0.05 g/l of acidic SLP; FIG. 6D shows the layer of white paint over the layer of primer with 0.1 g/l of acidic SLP or 0.5 g/l of acidic SLP; and FIG. 6E shows the layer of white paint over the layer of primer with 1 g/l of acidic SLP or 5 g/l of acidic SLP.

The sample drywall panel is evaluated visually to determine how much red paint is visible through the primed drywall or the primed and painted drywall. Most samples with a single layer of primer containing the added SLP performed better in blocking red paint bleeding than did the sample primer layers without SLP. When the layer of white paint was applied on top of the primer layer, the samples with the primers with added SLP performed better at blocking leeching of the red paint than did those samples that did not have SLP in the primer. Additionally, the sample with the lowest concentration (0.05 g/l) of either lactonic or acidic SLP performed best at limiting color bleeding. The control samples with no added SLP performed the poorest; the red color was still visible through layers of primer and paint. Adding either acidic or lactonic SLP to a conventional water-based primer can reduce paint color bleeding.

REFERENCES

Miranda-Villagómez, Iris, L., Gómez-Merino, Fernando Carlos, S.-V., Manuel, Sanchez-Garcia. & Ángel, M. (2019, November 18). Nanophosphorus Fertilizer Stimulates Growth and Photosynthetic Activity and Improves P Status in Rice.

Fairhurst, D., 2013. "An Overview of the Zeta Potential—Part 1: The Concept." American Pharmaceutical Review. https://www.americanpharmaceuticalreview.com/Featured-Articles/133232-An-Overview-of-the-Zeta-Potential-Part-1-The-Concept/(Accessed 3/22/21).

Fairhurst, D., 2013. "An Overview of the Zeta Potential—Part 2: Measurement." American Pharmaceutical Review. https://www.americanpharmaceuticalreview.com/Featured-Articles/134634-An-Overview-of-the-Zeta-Potential-Part-2-Measurement/(Accessed 3/22/21).

Fairhurst, D., 2013. "An Overview of the Zeta Potential—Part 3: Uses and Applications." American Pharmaceutical Review. https://www.americanpharmaceuticalreview.com/Featured-Artieles/139288-An-Overview-of-the-Zeta-Potential-Part-3-Uses-and-Applications/(Accessed 3/22/21).

What is claimed:

1. A method for dispersing nanoparticles in a primer, said method comprising:

adding to the primer a nanoparticle composition comprising a biosurfactant that is a glycolipid and one or more primer components wherein the nanoparticle composition comprises positively and negatively charged nanoparticles at a ratio of a 1:10 to 10:1, positively charged to negatively charged;

applying the primer to a surface; and applying a paint over the primer, wherein the primer is formulated with the biosurfactant to prevent color bleeding through the primer.

2. The method of claim 1, wherein the biosurfactant is a sophorolipid (SLP).

3. The method of claim 1, wherein the primer comprises one or more components selected from a binder, a solvent, a pigment or dye, a buffer, a resin, a stabilizer, and a pH modifier.

4. The method of claim 1, wherein the primer is formulated with the biosurfactant to increase adhesion to the surface.

5. The method of claim 1, further comprising measuring the degree of dispersion of the nanoparticles in the primer.

6. The method of claim 2, wherein the SLP is an acidic SLP.

7. The method of claim 2, wherein the SLP is a lactonic SLP.

8. The method of claim 1, wherein the biosurfactant is added at a concentration between about 0.05 gram per liter (g/L) of the primer and about 5 g/L.

9. The method of claim 8, wherein the concentration is about 0.05 g/L.

10. The method of claim 8, wherein the concentration is about 0.1 g/L.

11. The method of claim 8, wherein the concentration is about 0.5 g/L.

12. The method of claim 8, wherein the concentration is about 1 g/L.

13. The method of claim 8, wherein the concentration is about 5 g/L.

14. The method of claim 1, wherein the primer is formulated with the biosurfactant to increase concealment of topographic variations of the surface.

15. The method of claim 1, wherein the primer is formulated with the biosurfactant to improve sealing of pores of the surface.

16. The method of claim 1, wherein the primer is formulated with the biosurfactant to prevent odor dissemination.

17. The method of claim 1, wherein the primer is formulated with the biosurfactant to establish a tie-coat layer.

18. The method of claim 1, wherein the primer is formulated with the biosurfactant to prevent stain bleeding through the primer.

* * * * *